United States Patent [19]
Grethe et al.

[11] 3,931,193
[45] Jan. 6, 1976

[54] QUINUCLIDINE DERIVATIVES

[75] Inventors: Guenter Grethe, North Caldwell; Milan Radoje Uskokovic, Upper Montclair, both of N.J.

[73] Assignee: Hoffmann-La Roche Inc., Nutley, N.J.

[22] Filed: May 2, 1974

[21] Appl. No.: 466,355

Related U.S. Application Data

[60] Division of Ser. No. 166,583, July 27, 1971, Pat. No. 3,823,146, which is a continuation-in-part of Ser. No. 117,131, Feb. 19, 1971, abandoned, which is a continuation-in-part of Ser. No. 20,034, March 16, 1970, abandoned.

[52] U.S. Cl. .......................................... 260/293.53
[51] Int. Cl.$^2$ ...................................... C07D 453/02
[58] Field of Search ............................... 260/293.53

[56] References Cited
OTHER PUBLICATIONS
Chem. Abstracts, 53: 6278c, (1959).
Chem. Abstracts, 54: 22641a, (1960).

Primary Examiner—G. Thomas Todd
Attorney, Agent, or Firm—Samuel L. Welt; Bernard S. Leon; William G. Isgro

[57] ABSTRACT

Quinine, quinidine and analogs thereof, are prepared by reacting a 4-quinolyllithium compound with a 4,5-erythro-5-ethyl(or vinyl)-quinuclidine-2 ξ-carboxaldehyde or the corresponding quinuclidine-2-carboxylic acid alkyl ester. Also described, inter alia, is the preparation of a 4,5-erythro-5-ethyl(or vinyl)-quinuclidine-2 ξ-carboxaldehyde, and a 4,5-erythro-5-ethyl(or vinyl)-quinuclidine-2 ξ-carboxylic acid and esters thereof. The end products are useful as antimalarial and antiarrhythmic agents.

5 Claims, No Drawings

QUINUCLIDINE DERIVATIVES

CROSS-REFERENCE TO RELATED APPLICATIONS

This application is a division of U.S. Pat. application Ser. No. 166,583, filed July 27, 1971, now U.S. Pat. No. 3,823,146, which in turn is a continuation-in-part of U.S. Pat. application Ser. No. 117,131, filed Feb. 19, 1971, now abandoned, which in turn is a continuation-in-part of U.S. Pat. application Ser. No. 20,034, filed Mar. 16, 1970, now abandoned.

BRIEF SUMMARY OF THE INVENTION

The invention relates to the preparation of compounds of the formulas I and II

In one aspect, the invention relates to the preparation of compounds of formulas I and II, wherein $R_2$ is ethyl or vinyl, by a process which comprises reacting the mixture of epimeric 5(R)-ethyl(or vinyl)-4(S)-quinuclidine-2$\xi$-carboxaldehydes, enantiomers or racemates, with a 4-quinolyllithium compound.

In another aspect, the invention relates to the preparation of compounds of formulas I and II, wherein $R_2$ is ethyl or vinyl, by a process which comprises reacting the mixture of epimeric 5(R)-ethyl(or vinyl)-4(S)-quinuclidine-2$\xi$-carboxylic acid alkyl esters, enantiomers or racemates thereof, with a 4-quinolyllithium compound and thereafter reducing the resulting 4-[5(R)-ethyl(or vinyl)-4(S)-quinuclidin-2(R or S)ylcarbonyl]quinoline, its enantiomer or its racemate, to the corresponding end product of formulas I and II.

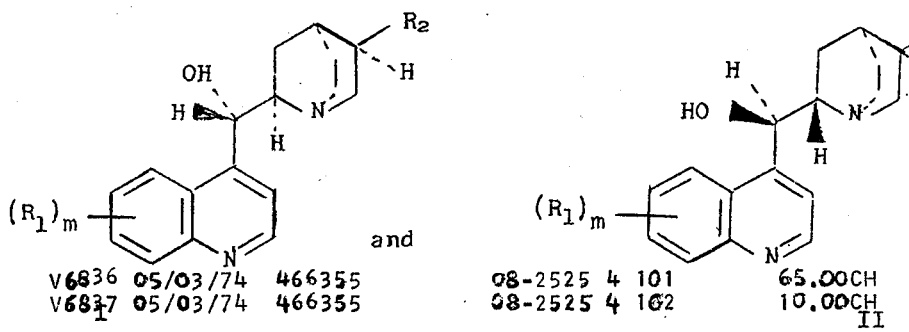

enantiomers and racemates thereof;

wherein $m$ is 1 or 2; $R_1$ is hydrogen, hydroxy, halogen, trifluoromethyl, lower alkyl, lower alkoxy, or when $m$ is 2, with an adjacent $R_1$, is also methylenedioxy; and $R_2$ is ethyl or vinyl.

In still another aspect, the invention relates to intermediates of the formulas:

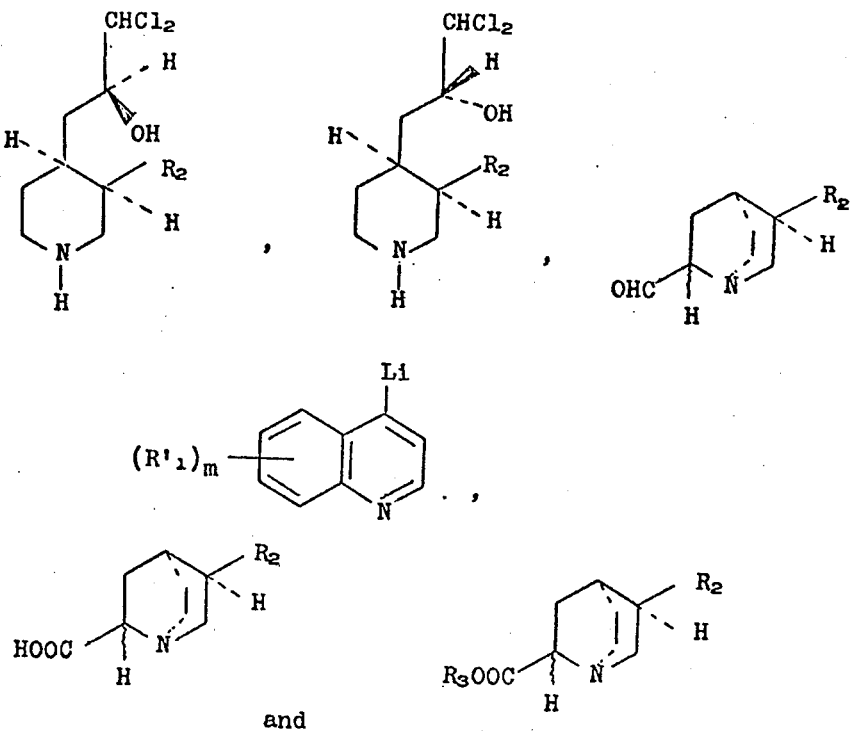

their racemates and enantiomers, wherein $R_2$ is as previously described, $R_3$ is lower alkyl, aryl or aryl-lower alkyl; $m$ is 1 or 2, and $R'_1$ is hydroxy, halogen, trifluoromethyl, lower alkyl or lower alkoxy, or when m is 2, with an adjacent $R_1$, is also methylenedioxy.

DETAILED DESCRIPTION OF THE INVENTION

The term "lower alkyl" as used herein denotes a hydrocarbon group containing 1–7 carbon atoms, such as methyl, ethyl, propyl, butyl and the like; methyl and ethyl are preferred. The term "lower alkoxy" denotes a lower alkyl ether group in which the lower alkyl moiety is as described above. The term "halogen" denotes all the halogens, i.e., bromine, chlorine, fluorine and iodine; chlorine is preferred. The term "aryl" denotes phenyl or phenyl bearing one or more substituents selected from the group consisting of halogen, trifluoromethyl, lower alkyl, lower alkoxy, nitro, amino, lower alkylamino and di-lower alkylamino. Exemplary of "aryl-lower alkyl" are benzyl, phenethyl and the like.

A process aspect of the invention is exemplified by Reaction Scheme Ia.

Scheme Ia wherein $R_3$ is lower alkyl, aryl or aryl-lower alkyl.

In Reaction Scheme Ia, the racemic 1,1,1-trichloro-3-(3-ethyl-4-pyridinyl)propan-2-ol of formula III [also known as 3-ethyl-4-(2-hydroxy-3,3,3-trichloropropyl)-pyridines] or either of its enantiomers is converted to the mixture of racemic, epimeric cis 1,1-dichloro-3-(3-ethyl-4-piperidinyl)propan-2ξ-ols of formulas IVa and Va or their corresponding enantiomers utilizing a hydrogenation catalyst, for example, a noble metal, such as palladium, platinum and rhodium; Raney nickel; and the like. The hydrogenation is conveniently carried out at room temperature or above room temperature, preferably at 60° and at a hydrogen pressure of about 1 atmosphere to about 100 atmospheres. Moreover, the hydrogenation can be suitably carried out in the presence of water and an inert organic solvent, for example, an alkanol, such as ethanol, methanol and the like, and in the presence of a mineral acid, such as hydrochloric, hydrobromic, sulfuric acid and the like, or an organic acid, such as acetic acid, tartaric acid and the like.

The enantiomers or racemates of epimeric cis 1,1-dichloro-3-(3-ethyl-4-piperidinyl)propan-2ξ-ols of for-

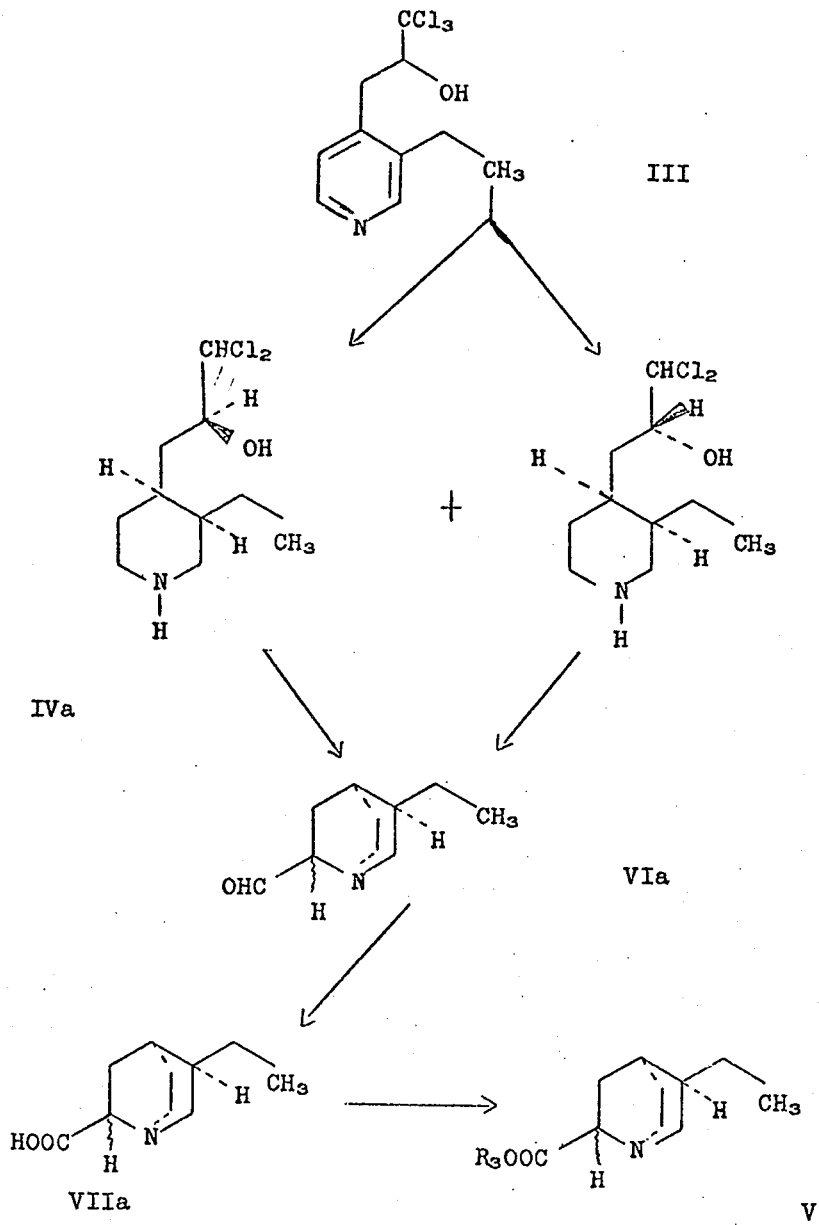

mulas IVa and Va are converted to the mixture of epimeric 5(R)-ethyl-4(S)-quinuclidine-2ξ-carboxaldehydes of formula VIa, enantiomers or racemates, utilizing a cyclizing and dehydrochlorinating agent. Exemplary of such agents are bases, for example, alkali metal hydroxides, such as sodium hydroxide and potassium hydroxide; alkali metal alkoxides, such as potassium t-butoxide; and basic anion exchange resins, such as Amberlite anion exchange resin IRA-401 (OH) and the like. The reaction is conveniently carried out at room temperature; however, higher or lower temperatures may also be utilized. Moreover, the reaction can be suitably carried out in the presence of an inert organic solvent, for example, an alkanol, such as methanol, ethanol and the like; a hydrocarbon, such as benzene, toluene, hexane, petroleum ether and the like; or an ether, such as tetrahydrofuran, diethylether, dioxane and diglyme; or a mixture of water and an immiscible inert organic solvent, such as benzene, dichloromethane or the like.

The mixture of epimeric 5(R)-ethyl-4(S)-quinuclidine-2ξ-carboxyaldehydes of formula VIa, enantiomers or racemates, is converted to the mixture of epimeric 5(R)-ethyl-4(S)-quinuclidine-2ξ-carboxylic acids of formula VIIa, enantiomers or racemates, utilizing an oxidizing agent. As the oxidizing agent, there can be utilized silver oxide, chromic acid, potassium permanganate, and the like. The oxidation is conveniently carried out at room temperature or below, and if desired, in the presence of a solvent such as an alkanol or water.

The mixture of epimeric 5(R)-ethyl-4(S)-quinuclidine-2ξ-carboxylic acids of formula VIIa, enantiomers or racemates, is converted to the mixture of epimeric 5(R)-ethyl-4(S)-quinuclidine-2ξ-carboxylic acid alkyl esters of formula VIIIa, enantiomers or racemates, utilizing an esterifying agent. As the esterifying agent, there can be utilized alkanols such as ethanol, methanol, and the like, in the presence of an acid such as hydrogen chloride, sulfuric acid and the like. The esterification is conveniently carried out at a temperature in the range of between about room temperature and the boiling temperature of the reaction mixture.

Still another process of the invention is exemplified by Reaction Scheme Ib:

Scheme Ib

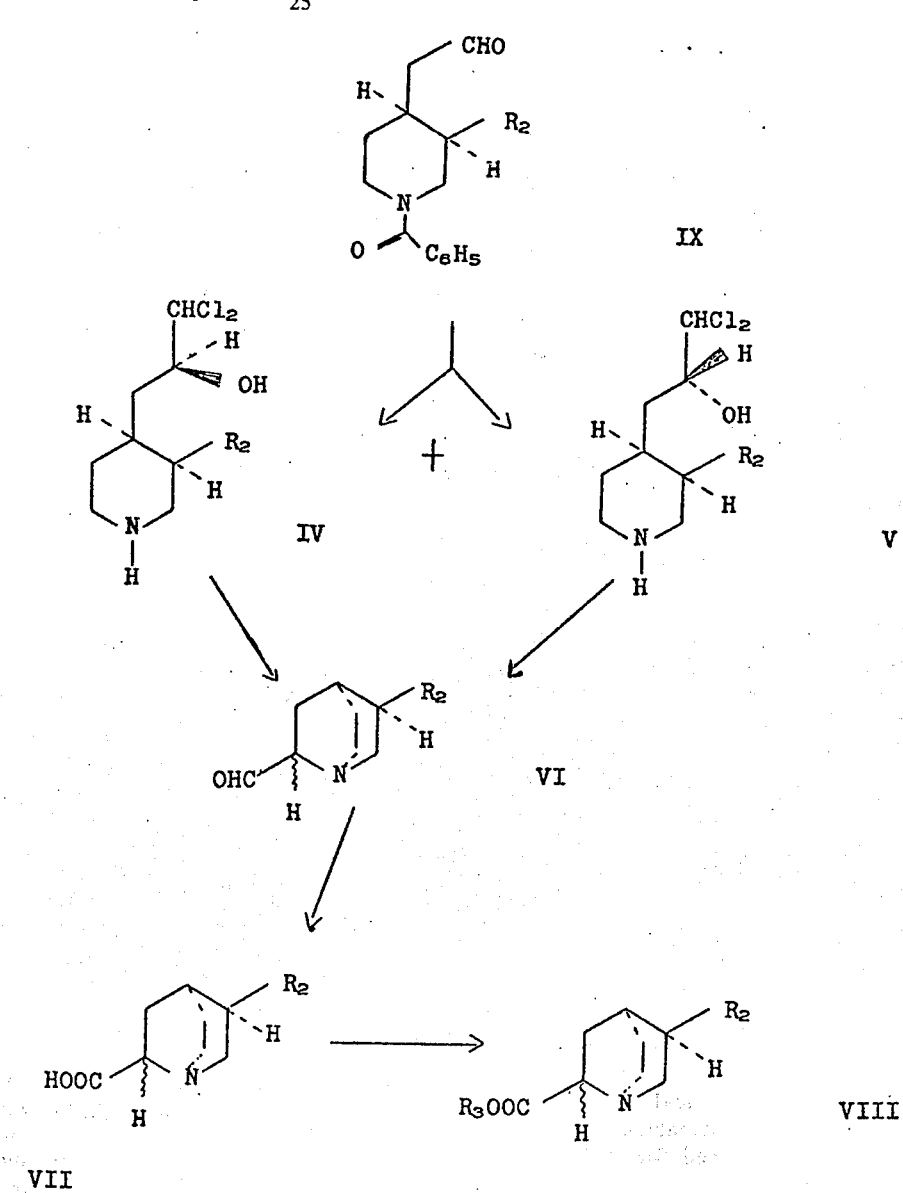

wherein R₂ and R₃ are as previously described.

In Reaction Scheme Ib the N-benzoyl-3(R)-ethyl(or vinyl)-4(S)-piperidineacetaldehyde of formula IX, its A further process aspect of the invention is exemplified by Reaction Scheme II:

Scheme II

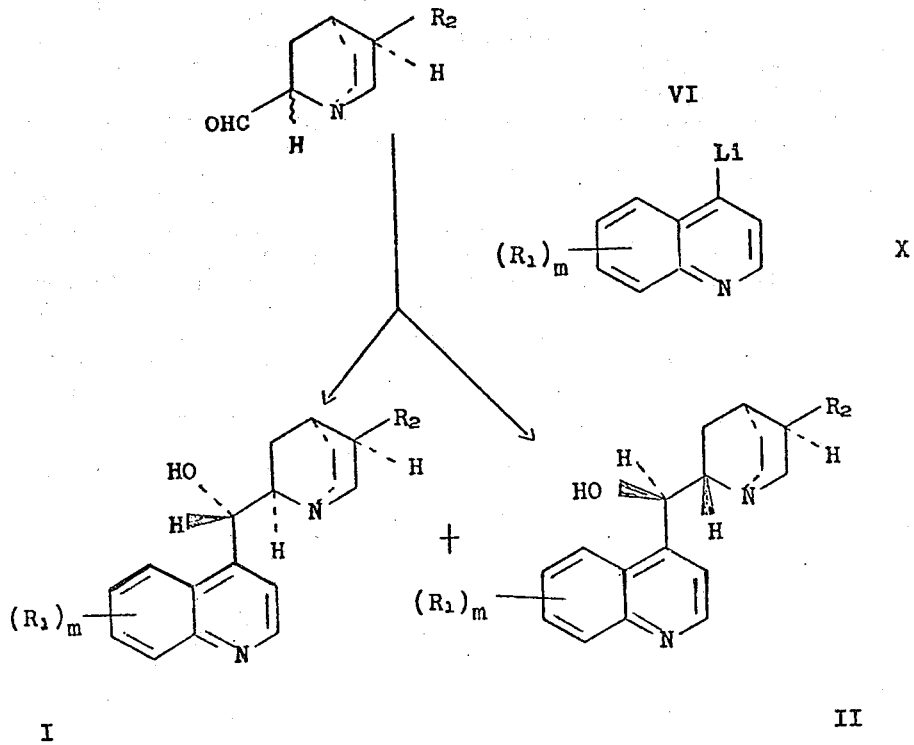

enantiomer or racemate, is converted to the corresponding mixture of epimeric 1,1-dichloro-3-[3(R)-ethyl(or vinyl)-4(S)-piperidinyl]propan-2ξ-ols of formulas IV and V, enantiomers or racemates, utilizing a Grignard reagent, such as dichloromethyllithium. The reaction is conveniently carried out at room temperature and below room temperature, preferably between about 0° and about −70°C. Moreover, the reaction can be suitably carried out in the presence of an inert organic solvent, for example, an ether, such as tetrahydrofuran, diethylether, dioxane and diglyme; or a hydrocarbon such as benzene, toluene, hexane, petroleum ether and the like.

The mixture of epimeric 1,1-dichloro-3-[3(R)-ethyl(or vinyl)-4(S)-piperidinyl]propan-2ξ-ols of formulas IV and V, enantiomers or racemates, are converted to the mixture of epimeric 5(R)-ethyl(or vinyl)-4(S)-quinuclidine-2ξ-carboxaldehydes of formula VI, enantiomers or racemates, by the procedure previously described for the compounds of formulas IVa and Va.

The mixture of epimeric 5(R)-ethyl(or vinyl)-4(S)-quinuclidine-2ξ-carboxaldehydes of formula VI, enantiomers or racemates, is converted to the mixture of epimeric 5(R)-ethyl(or vinyl)-4(S)-quinuclidine-2ξ-carboxylic acids of formula VII, enantiomers or racemates, by the procedure previously described for the compound of formula VIa.

The mixture of epimeric 5(R)-ethyl(or vinyl)-4(S)-quinuclidine-2ξ-carboxylic acids of formula VII, enantiomers or racemates thereof, is converted to the mixture of epimeric 5(R)-ethyl(or vinyl)-4(S)-quinuclidine-2ξ-carboxylic acid alkyl esters of formula VIII, enantiomers or racemates thereof, by the procedure previously described for the compound of formula VIIa.

enantiomers and racemates thereof, wherein R₁, R₂ and m are as previously described.

In Reaction Scheme II, the mixture of epimeric 5(R)-ethyl (or vinyl)-4(S)-quinuclidine-2ξ-carboxaldehydes of formula VI, enantiomers or racemates thereof, is reacted with a 4-quinolyllithium compound of formula X to yield the corresponding α(S)-[5(R)-ethyl(or vinyl)-4(S)-quinuclidin-2(R)-yl]-4-quinoline-methanol of formula I, enantiomer or racemate thereof, and α(R)-[5(R)-ethyl(or vinyl)-4(S)-quinuclidin-2(S)-yl]-4-quinolinemethanol of formula II, enantiomer or racemate thereof. The 4-quinolyllithium compound of formula X is reacted in equimolar or greater than equimolar proportions with the compound of formula VI. Preferably, two molar proportions of the quinolyllithium compound are utilized. The reaction is conveniently carried out at room temperature or below room temperature, preferably at a temperature in the range of between about 0° and about −70°, in the presence of an inert organic solvent, for example, an ether, such as diethylether, tetrahydrofuran, dioxane and diglyme; or a hydrocarbon, such as benzene, toluene and the like. The reaction is conveniently carried out in the presence of complexing agents such as 1,4-diazabicyclo[2.2.2] octane or tetramethylethylenediamine.

Representative of the compounds of formula X are the following:

4-quinolyllithium;
6-methoxy-4-quinolyllithium;
6-methyl-4-quinolyllithium;
7-methoxy-4-quinolyllithium;
6,7-dimethoxy-4-quinolyllithium;
6,7-methylenedioxy-4-quinolyllithium;
6,8-dimethoxy-4-quinolyllithium;
6-chloro-4-quinolyllithium;

7-trifluoromethyl-4-quinolyllithium;
7-chloro-4-quinolyllithium;
6,8-dichloro-4-quinolyllithium; and the like.

Since the foregoing 4-quinolyllithium compounds are highly labile, it is preferred to prepare them in situ, by reacting the corresponding 4-bromoquinoline with, for example, n-butyllithium in the presence of a solvent, for example, a hydrocarbon, such as benzene, toluene, hexane, petroleum ether; or an ether, such as dioxane, ether, diglyme, tetrahydrofuran and the like. Exemplary of the 4-bromoquinoline compounds are:

4-bromoquinoline;
4-bromo-6-methoxyquinoline;
4-bromo-6-methylquinoline;
4-bromo-7-methoxyquinoline;
4-bromo-6,7-dimethoxyquinoline;
4-bromo-6,7-methylenedioxyquinoline;
4-bromo-6,8-dimethoxyquinoline;
4-bromo-6-chloroquinoline;
4-bromo-7-chloroquinoline;
4-bromo-6,8-dichloroquinoline;
4-bromo-7-trifluoromethylquinoline; and the like.

The 4-halo-quinolines can be prepared by known procedures from the corresponding 4-hydroxy-quinolines, exemplary of which are:

4-hydroxyquinoline;
4-hydroxy-6-methoxyquinoline;
4-hydroxy-6-methylquinoline;
4-hydroxy-7-methoxyquinoline;
4-hydroxy-6,7-dimethoxyquinoline;
4-hydroxy-6,7-methylenedioxyquinoline;
4-hydroxy-7-trifluoromethylquinoline;
4-hydroxy-6,8-dimethoxyquinoline;
4-hydroxy-6-chloroquinoline;
4-hydroxy-7-chloroquinoline;
4-hydroxy-6,8-dichloroquinoline; and the like.

Yet another aspect of the invention is exemplified by Reaction Scheme III.

Scheme III

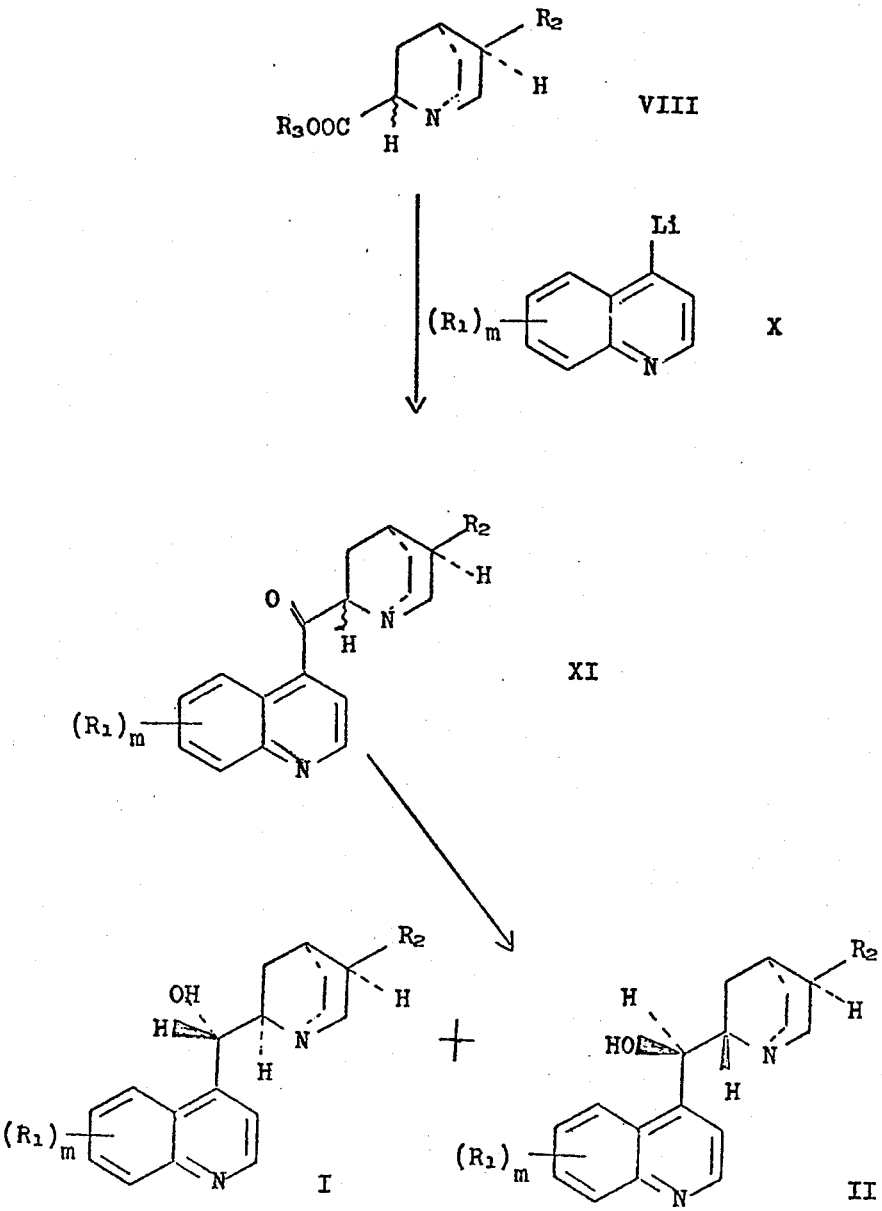

wherein $R_1$, $R_2$, $R_3$ and $m$ are as previously described.

In Reaction Scheme III, the mixture of epimeric 5(R)-ethyl-(or vinyl)-4(S)-quinuclidine-2$\xi$-carboxylic acid alkyl esters of formula VIII, enantiomers or racemates, is reacted with a 4-quinolyllithium compound of formula X to yield the corresponding mixture of epimeric 4-[5(R)-ethyl(or vinyl)-4(S)-quinuclidin-2$\xi$-ylcarbonyl]quinolines of formula XI, enantiomers or racemates thereof. The 4-quinolyllithium compound of formula X is reacted in equimolar or greater than equimolar proportions with the compound of formula VIII. Preferably, two molar proportions of the quinolyllithium compound are utilized. The reaction is conveniently effected at room temperature or below room temperature, preferably in the range of about between 0° and about −70°C. Suitably, an inert solvent, for example, an ether, such as diethyl ether, tetrahydrofuran, dioxane and diglyme, or a hydrocarbon such as benzene, toluene, and the like, may be utilized. Further, the reaction may be conveniently carried out in the presence of complexing agents such as 1,4-diazabicyclo[2.2.2] octane or tetramethylethylenediamine.

The conversion of the mixture of epimeric 4-[5(R)-ethyl(or vinyl)-4(S)-quinuclidin-2$\xi$-ylcarbonyl]quinolines of formula XI, enantiomers or racemates thereof, to $\alpha$(S)-[5(R)-ethyl(or vinyl)-4(S)-quinuclidin-2(R)-yl]-4-quinolinemethanols of formula I, enantiomer or racemate thereof, and to $\alpha$(R)-[5(R)-ethyl(or vinyl)-4(S)-quinuclidin-2(S)-yl]-4-quinolinemethanols of formula II, enantiomer or racemate, respectively, is carried out utilizing a stereoselective reducing agent, for example, a dialkylaluminum hydride, such as diisobutylaluminum hydride or the like. The reduction is suitably carried out at room temperature; however, temperatures above or below room temperature may be employed. It is preferred to employ a temperature between 20°C. and 50°C. The reduction can be conveniently conducted in the presence of an inert organic solvent, for example, a hydrocarbon such as benzene or toluene, or an ether such as diethylether, tetrahydrofuran or the like.

The conversion of the compounds of formula XI, enantiomers or racemates thereof, to those of formulas I and II, enantiomers or racemates thereof, respectively, when $R_2$ is ethyl, can also be effected utilizing a hydrogenation catalyst such as nickel, palladium, ruthenium, copper or barium chromite in the presence of a solvent, for example, an aqueous or non-aqueous alkanol such as methanol or ethanol, or an ether such as dioxane. When $R_2$ is ethyl or vinyl, the conversion can be effected utilizing a hydrogenation agent such as aluminum in ethanol, sodium isopropoxide in toluene, sodium or potassium borohydride in methanol, ethanol, isopropanol or tetrahydrofuran, lithium aluminum hydride, aluminum hydride, chloroaluminum hydride, dichloroaluminum hydride, bromoaluminum hydride, dibromoaluminum hydride, lithium tri-tert.-butoxyaluminum hydride in ether, tetrahydrofuran, dioxane or the like.

The compounds of formulas I and II and their pharmaceutically acceptable acid addition salts possess antimalarial and antiarrhythmic properties and are therefore useful as antimalarial and antiarrhythmic agents. Their pharmacologically useful anti-arrhythmic activity is demonstrated in warm-blooded animals utilizing standard procedures, for example, the test compound is administered to prepared mongrel dogs. The chest cavity of the experimental animal previously anesthetized using a combination of sodium barbitol, 300 mg/kg. and pentobarbitol, 15 mg/kg., i.v., is opened up through the third right interspace under artificial respiration and the pericardium is cut and sutured to the wall of the thorax so as to maintain the heart in a pericardial cradle throughout the course of the test procedure. Arterial pressure is monitored by inserting a polyethylene cannula into the aorta via the left carotid artery and is measured with an appropriate Statham pressure transducer. During the course of the experiment, electrical activity of the heart is viewed both on an oscilloscope and recorded on a Sanborn polyviso using standard ECG lead II. The heart is also observed visually. The antiarrhythmic assay of the test drug is undertaken using a modification of the method of Scherf and Chick, Circulation, 3, 764-769 (1951). A dripping of 1 percent solution of acetylcholine is applied to the sinus node and the atrium is irritated by pinching with a pair of forceps. This procedure produces a continuous atrial arrhythmia which mostly consists of atrial fibrillation. Since hypokalemia produces a susceptibility to atrial fibrillation (Leveque, Arch. Int. Pharmacodyn, 149, 297-307, 1964), 2 units/kg. of insulin is administered 30 minutes before the start of the acetylcholine drip. Once atrial fibrillation is established, there is a tenminute waiting period before the test drug is administered. The test drugs are administered intravenously at the rate of 1 mg/kg/minute until normal sinus rhythm appears or until 30 mg/kg. of drug is administered.

The pharmacologically useful antimalarial activity of the aforementioned compounds is demonstrated in warm-blooded animals using standard procedures, for example, the test substance is administered to albino mice in variable amounts. Albino mice are inoculated with about 10 million red cells infected with P. Berghei. Treatment is started on the first day after inoculation, and the drug is administered "per os" during 4 consecutive days. On the seventh day of infection, smears are made, stained with giemsa and microscopically examined for P. Berghei.

When racemic 7'-methoxy-dihydrocinchonidine dihydrochloride and racemic 7'-methoxy-dihydrocinchonine dihydrochloride are utilized as the test substance at dosages in the range of 125 mg/kg. to about 250 mg/kg., the microscopical examination of the blood smears is free of P. Berghei (negative).

The compounds of formulas I and II, which include qunine and quinidine and their dihydro- analogs, have effects quantitatively similar, for example, to those of quinine and quinidine of known therapeutic uses and properties. Thus, the compounds prepared by the process of the invention demonstrate a pattern of activity associated with antimalarials and antiarrhythmics of known efficacy and safety.

The compounds of formulas I and II form pharmaceutically acceptable acid addition salts and such salts are also within the scope of this invention. Thus, the aforementioned compounds form pharmaceutically acceptable addition salts with, for example, both pharmaceutically acceptable organic and inorganic acids, such as acetic acid, succinic acid, formic acid, methanesulfonic acid, p-toluene-sulfonic acid, hydrochloric acid, nitric acid, phosphoric acid, sulfuric acid and the like.

The products of the process of the invention can be incorporated into standard pharmaceutical dosage forms, for example, they are useful for oral or parenteral application with the usual pharmaceutical adjuvant materials, e.g., organic or inorganic inert carrier materials such as water, gelatin, lactose, starch, magnesium stearate, talc, vegetable oils, gums, polyalkyleneglycols, and the like. The pharmaceutical preparations can be employed in a solid form, e.g., as tablets, troches, suppositories, capsules, or in liquid form, e.g., as solutions, suspensions or emulsions. The pharmaceutical adjuvant materials can include preservatives, stabilizers, wetting or emulsifying agents, salts to change the osmotic pressure or to act as buffers. They can also contain other therapeutically active materials.

The following examples further illustrate the invention. All temperatures are in degrees centigrade, unless otherwise mentioned.

EXAMPLE 1

Preparation of 6,7-methylenedioxy-4-quinolinol

A suspension of 50 g. of 4-hydroxy-6,7-methylenedioxyquinoline-3-carboxylic acid in 500 ml. of freshly distilled quinoline was heated at 200° until the evolution of gas ceased. The reaction mixture was cooled to room temperature, diluted with an equal amount of ether and kept cool overnight. The precipitated brown solid (51.4 g., m.p. 254°–267°) was collected by filtration and dissolved in refluxing ethanol. The insoluble material was removed and the ethanol solution was reduced to one-third of its volume. The solution was diluted with an equal amount of ether. On cooling, 31.1 g. of 6,7-methylenedioxy-4-quinolinol separated, m.p. 280°–282°. Recrystallization (2x) from hot water yielded analytically pure 6,7-methylenedioxy-4-quinolinol as a pale yellow solid, m.p. 288°–289°.

Analysis Calcd. for $C_{10}H_7NO_3$ (189.16): C, 63.49; H, 3.73; N, 7.41. Found: C, 63.58; H, 4.04; N, 7.34.

EXAMPLE 2

Preparation of 4-bromo-6,7-methylenedioxyquinoline

To a slurry of 10 g. of 6,7-methylenedioxy-4-quinolinol and 10 ml. of phosphorus tribromide, preheated to 60°, was added 4 ml. of phosphorus oxybromide. The mixture was heated at 150°. After 1 hour, an additional 4 ml. phosphorus oxybromide was added and heating was continued for 2 hours with occasional stirring. The mixture was cooled to room temperature and carefully added to 1 l. of vigorously stirred crushed ice. The precipitate was collected by filtration and, after washing with water, was suspended in 100 ml. of water. The suspension was rendered alkaline by the addition of solid sodium bicarbonate. The precipitate was collected by filtration, washed with water and extracted thoroughly with chloroform. The organic extract was dried over sodium sulfate and evaporated to dryness to yield a nearly colorless solid which on sublimation at 100°–120° and 0.35 mmHg gave 8.3 g. of 4-bromo-6,7-methylenedioxyquinoline, m.p. 147°–149°.

Analysis Calcd. for $C_{10}H_6BrNO_2$ (252.08): C, 47.65; H, 2.40; N, 5.56. Found: C, 47.57; H, 2.30; N, 5.42.

EXAMPLE 3

Preparation of 4-bromo-6,8-dichloroquinoline

A paste prepared from 33 g. of 6,8-dichloro-4-quinolinol and 50 ml. of phosphorus tribromide was heated to 60°. After adding 20 ml. (56 g.) of phosphorus oxybromide, the mixture was maintained at 150° for 3 hours with occasional stirring. Then, the mixture was cooled and added carefully to 1.5 l. of vigorously stirred crushed ice. The aqueous suspension was rendered alkaline by the addition of 12N sodium hydroxide. The precipitate which formed was collected by filtration and dried in a vacuum oven. Sublimation of the dried material at 140° and 0.3 mmHg yielded 35.7 g. of crystalline 4-bromo-6,8-dichloroquinoline, m.p. 163°–165°. Recrystallization from ether gave pure 4-bromo-6,8-dichloroquinoline, m.p. 164°–166°.

Analysis Calcd. for $C_9H_4BrCl_2N$ (276.97): C, 39.03; H, 1.46; H, 5.05; Cl, 25.60. Found: C, 39.03; H, 1.32; N, 5.04; Cl, 25.61.

EXAMPLE 4

Preparation of
1,1,1-trichloro-3-(3-ethyl-4-pyridinyl)propan-2(R)-ol
and
1,1,1-trichloro-3-(3-ethyl-4-pyridinyl)propan-2(S)-ol To 106.6 g. of 1,1,1-trichloro-3-(3-ethyl-4-pyridinyl)propan-2-ol dissolved in 1.2 l. of hot acetone was added a solution of 65.2 g. of d-tartaric acid in 1 l. of acetone. Upon cooling, crystalline material separated (66.8 g.) which after fractional crystallization from acetone, yielded pure 1,1,1-trichloro-3-(3-ethyl-4-pyridinyl)propan-2(R)-ol d-tartrate, m.p. 176°–177.5°, $[\alpha]_D^{25}$ +30.7° (c 0.960, ethanol)

Analysis Calcd. for $C_{10}H_{12}Cl_3NO \cdot C_4H_6O_6$ (418.67): C, 40.16; H, 4.33; N, 3.35; Cl, 25.40. Found: C, 39.97; H, 4.18; N, 3.23; Cl, 25.59.

The tartrate salt was dissolved in water. The solution was rendered alkaline with a saturated aqueous solution of sodium carbonate and extracted four times with dichloromethane. The combined organic extracts were dried over sodium sulfate and evaporated to dryness under reduced pressure to give 1,1,1-trichloro-3-(3-ethyl-4-pyridinyl)propan-2(R)-ol, m.p. 132°–134°, $[\alpha]_D^{25}$ +45.1° (c 1.025, ethanol) after recrystallization from ether.

Analysis Calcd. for $C_{10}H_{12}Cl_3NO$ (268.58): C, 44.72; H, 4.51; N, 5.22; Cl, 39.60. Found: C, 44.99; H, 4.59; N, 4.96; Cl, 39.62.

The mother liquors obtained from the fractional crystallization were combined and evaporated to dryness. The resulting residue was dissolved in 4 l. of water. Insoluble material was removed by filtration, and the solution was rendered alkaline with 6N sodium hydroxide. The resulting solution was extracted three times with dichloromethane. The combined organic extract was washed three times with water, dried over sodium sulfate and evaporated to dryness to give 57.2 g. of a brown solid. A solution of this material in 800 ml. of acetone was combined with a solution of 31.8 g. of l-tartaric acid in 700 ml. of acetone. Upon cooling, 54.9 g. of crystalline tartrate separated. Fractional crystallization of this material from acetone yielded pure 1,1,1-trichloro-3-(3-ethyl-4-pyridinyl)propane-2(S)-ol l-tartrate, m.p. 177°–178°, $[\alpha]_D^{25}$ −30.3° (c 1.065, ethanol).

Analysis Calcd. for $C_{10}H_{12}Cl_3NO \cdot C_4H_6O_6$ (418.67): C, 40.16; H, 4.33; N, 3.35; Cl, 25.40. Found: C, 39.83; H, 4.63; N, 3.29; Cl, 25.32.

Pure 1,1,1-trichloro-3-(3-ethyl-4-pyridinyl)propan-

2(S)-ol obtained from 1,1,1-trichloro-3-(3-ethyl-4-pyridinyl)propan-2(S)-ol 1-tartrate, as described above for the preparation of the other enantiomer had a melting point of 132°–134°, $[\alpha]_D^{25}$ −45.5° (c, 1.020, ethanol) after recrystallization from ether.

Analysis Calcd. for $C_{10}H_{12}Cl_3NO$ (268.58): C, 44.72; H, 4.51; N, 5.22; Cl, 39.60, Found: C, 45.05; H, 4.51; N, 5.04; Cl, 39.32.

H, 7.29; Cl, 38.55; N, 5.06. Found: C, 43.38; H, 7.41; Cl, 38.37; N, 4.86.

EXAMPLE 6

Preparation of
1,1-dichloro-3-[3(S)-ethyl-4(R)-piperidinyl]-propan-2(R)-ol hydrochloride (A) and
1,1-dichloro-3-[3(R)-ethyl-4(S)-piperidinyl]propan-2(R)-ol hydrochloride (B)

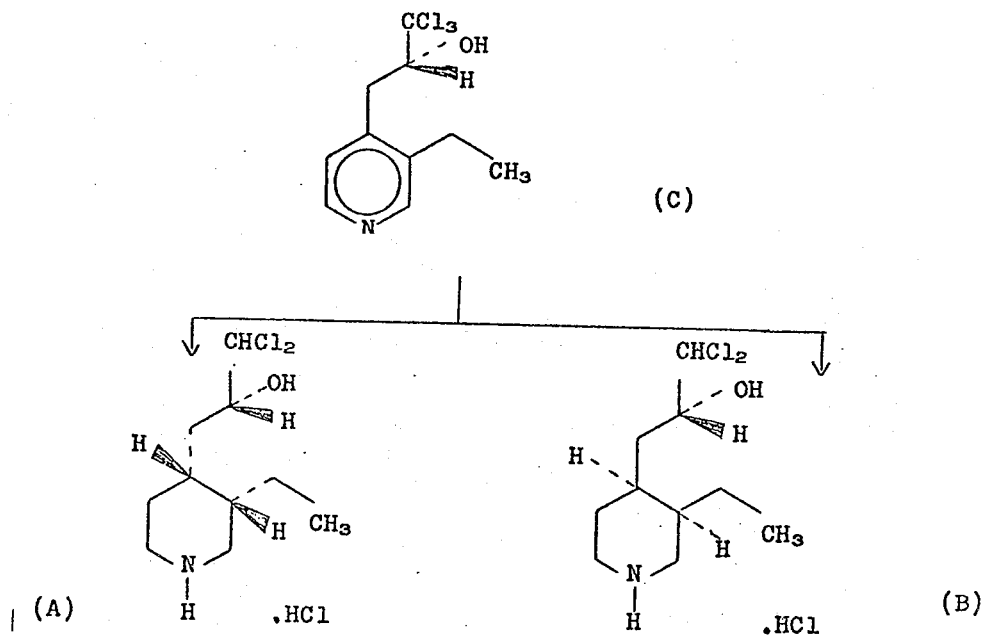

EXAMPLE 5

Preparation of racemic
1,1-dichloro-3-[3]-3(R)-ethyl-4(S)-piperidinyl]propan-2(S)-ol hydrochloride and racemic
1,1-dichloro-3-[3(R)-ethyl-4(S)-piperidinyl]propan-2(R)-ol hydrochloride To a solution containing 26.85 g. of racemic 1,1,1-trichloro-3-(3-ethyl-4-pyridinyl)propan-2-ol in 400 ml. of 5 percent aqueous hydrochloric acid was added 4 g. of platinum dioxide and the mixture was hydrogenated at 60°C. and 67 atmospheres of pressure. After cooling to room temperature, the catalyst was removed by filtration, and the resulting filtrate was evaporated in vacuo. The residue was crystallized from 70 ml. of absolute ethanol to give 10.5 g. (38 percent) of racemic 1,1-dichloro-3-[3(R)-ethyl-4(S)-piperidinyl]propan-2(S)-ol hydrochloride, having a melting point of 200°–205°, after recrystallization, m.p. 205°–209°.

Analysis Calcd. for $C_{10}H_{20}Cl_3NO$ (276.64): C, 43.42; H, 7.29; Cl, 38.55; N, 5.06. Found: C, 43.69; H, 7.25; Cl, 38.35; N, 5.22.

Crystallization of the mother liquors from 30 ml. of acetone gave 9.5 g. (34.5 percent) of racemic 1,1-dichloro-3-[3(R)-ethyl-4(S)-piperidinyl]propan-2(R)-ol hydrochloride, having a melting point of 123°–129° after two recrystallizations, m.p. 132°–134°.

Analysis Calcd. for $C_{10}H_{20}Cl_3NO$ (276.64) C, 43.42;

A solution of 2.7 g. of 1,1,1-trichloro-3-(3-ethyl-4-pyridinyl)propan-2(R)-ol (C) in 40 ml. of 5 percent aqueous hydrochloric acid was hydrogenated over 0.4 g. of platinum oxide at 60°–90° and 65 atmospheres of pressure. After cooling to room temperature, the catalyst was removed by filtration, and the resulting filtrate was evaporated under reduced pressure. The residue was crystalized from 40 ml. of ethanol to give 600 mg. of 1,1-dichloro-3-[3(S)-ethyl-4(R)-piperidinyl]propan-2(R)-ol hydrochloride, m.p. 232°–233°, $[\alpha]_D^{25}$ +29.63° (c 1.0953, methanol) after recrystallization from ethanol.

Analysis Calcd. for $C_{10}H_{19}Cl_2NO·HCl$ (276.65): C, 43.42; H, 7.28; N, 5.06. Found: C, 43.11; H, 7.32; N, 4.98.

The mother liquors were concentrated and crystallization of the residue from acetone gave 557 mg. of 1,1-dichloro-3-[3(R)-ethyl-4(S)-piperidinyl]propan-2(R)-ol hydrochloride, m.p. 168°–170°, $[\alpha]_D^{25}$ +25.25° (c 1.0140, methanol), after recrystallization from acetone.

Analysis Calcd. for $C_{10}H_{19}Cl_2NO·HCl$ (276.65): C, 43.42; H, 7.78; N, 5.06. Found: C, 43.55; H, 7.47; N, 5.00.

EXAMPLE 7

Preparation of
1,1-dichloro-3-[3(R)-ethyl-4(S)-piperidinyl]propan-2(S)-ol hydrochloride (D) and
1,1-dichloro-3-[3(S)-ethyl-4(R)-piperidinyl]propan-2(S)-ol hydrochloride (E)

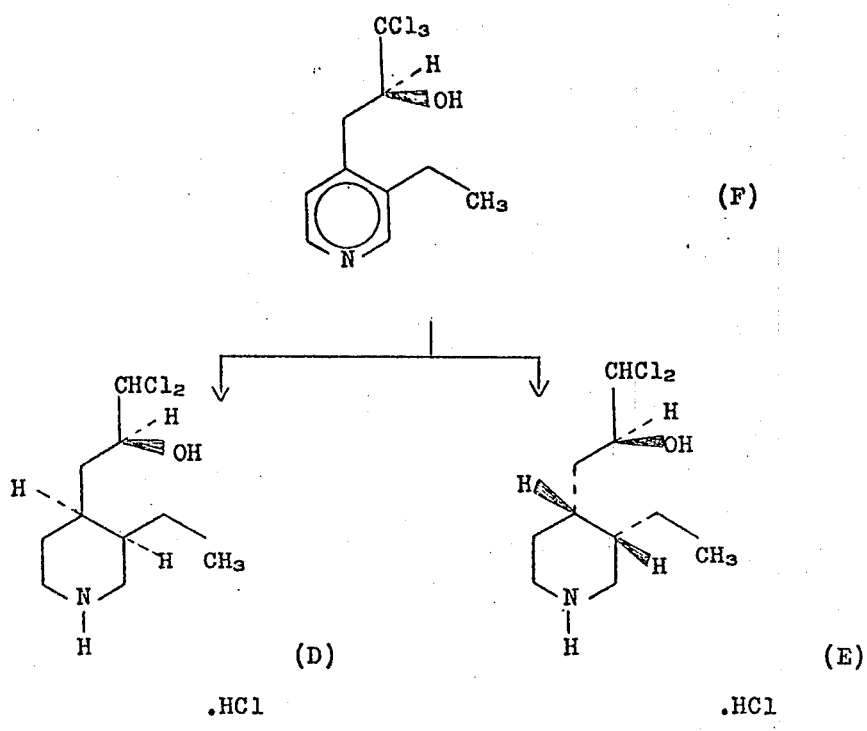

A solution of 2.7 g. of 1,1,1-trichloro-3-(3-ethyl-4-pyridinyl)propan-2(S)-ol (F) in 40 ml. of 5 percent aqueous hydrochloric acid was hydrogenated over 0.4 g. of platinum oxide at 60° and 65 atmospheres of pressure. After cooling to room temperature, the catalyst was removed by filtration, and the filtrate was concentrated under reduced pressure. The residue was crystallized from 20 ml. of ethanol to give 600 mg. of 1,1-dichloro-3-[3(R)-ethyl-4(S)-piperidinyl]propan-2(S)-ol hydrochloride, m.p. 227°–229°. Several recrystallizations from ethanol yielded pure 1,1-dichloro-3-[3(R)-ethyl-4(S)-piperidinyl]-propan-2(S)-ol hydrochloride, m.p. 232-233°, $[\alpha]_D^{25}$ −28.3° (c 1.0237, methanol).

Analysis Calcd. for $C_{10}H_{19}Cl_2NO \cdot HCl$ (276.65): C, 43.42; H, 7.28; N, 5.06. Found: C, 43.58; H, 7.32; N, 5.08.

The free base obtained from 1,1-dichloro-3-[3(R)-ethyl-4(S)-piperidinyl]propan-2(S)-ol hydrochloride on treatment with aqueous potassium carbonate and extraction with dichloromethane, was combined with ethanolic hydrogen bromide to give 1,1-dichloro-3-[3(R)-ethyl-4(S)-piperidinyl]propan-2(S)-ol hydrobromide, m.p. 223°–224°, $[\alpha]_D^{25}$ −24.77° (c, 0.9486, methanol), after several recrystallizations from ethanol.

Analysis Calcd. for $C_{10}H_{19}Cl_2NO \cdot HBr$ (321.11): C, 37.41; H, 6.28; N, 4.36. Found: C, 37.71; H, 6.44; N, 4.46.

The mother liquors obtained from the crystallization of 1,1-dichloro-3-[3(R)-ethyl-4(S)-piperidinyl]propan-2(S)-ol hydrochloride were combined and concentrated under reduced pressure. The residue was triturated with acetone and the crystalline material was recrystallized from acetone to give 729 mg. of 1,1-dichloro-3-[3(S)-ethyl-4(R)-piperidinyl]propan-2(S)-ol hydrochloride. Recrystallization from acetone yielded 1,1-dichloro-3-[3(S)-ethyl-4(R)-piperidinyl]-propan-2(S)-ol hydrochloride, m.p. 169.5°–171.5°, $[\alpha]_D^{25}$ −25.15° (c 0.9306, methanol).

Analysis Calcd. for $C_{10}H_{19}Cl_2NO \cdot HCl$ (276.65): C, 43.42; H, 7.28; N, 5.06. Found: C, 43.69; H, 7.49; N, 5.34.

EXAMPLE 8

Preparation of
1,1-dichloro-3-[3(R)-vinyl-4(S)-piperidinyl]-propan-2(S)-ol hydrochloride and
1,1-dichloro-3-[3(R)-vinyl-4(S)-piperidinyl]propan-2(R)-ol hydrochloride To a solution containing 3.07 ml. of methylene chloride in 60 ml. of anhydrous tetrahydrofuran cooled to −70°, there was added over a period of 1 hour 44 mmoles of n-butyllithium in 28 ml. of hexane under an atmosphere of dry nitrogen. Stirring of the mixture at the same temperature was continued for 20 minutes and then followed by the dropwise addition of 5.19 g. (20 mmoles) of 2-[1-benzoyl-3(R)-vinyl-4(S)-piperidinyl]acetaldehyde in 30 ml. of anhydrous tetrahydrofuran. After 30 minutes, the reaction was quenched by the addition of 30 ml. of water. The mixture was allowed to warm up to room temperature and was subsequently extracted three times with ether. The combined ether extracts were washed with water, dried over sodium sulfate and evaporated to dryness. The residue was dissolved in 80 ml. of 3N hydrochloric acid. The acidic solution was washed with ether and neutralized with 3N sodium hydroxide. The solution was washed with ether, rendered alkaline by the addition of 3N sodium hydroxide and extracted with ether. The ether extract was washed with water, dried over sodium sulfate and evaporated to dryness. The residue (3.8 g.) was dissolved in ethanol and treated with an excess of ethanolic hydrogen chloride. The solvent was evaporated under reduced pressure and the resulting solid residue was crystallized from ethanol to give 2.0 g. of a mixture of epimeric 1,1-dichloro-3-[3(R)-vinyl-4(S)-piperidinyl]propan-2$\xi$-ol hydrochlorides. Fractional crystallization from ethanol followed by recrystallization of the combined fractions from ethanol gave 1,1-dichloro-3-[3(R)-vinyl-4(S)-piperidinyl]propan-2(S)-ol hydrochloride, m.p. 225-225.5°, $[\alpha]_D^{25}$ −13.3° (c 1.02, methanol).

Analysis Calcd. for $C_{10}H_{17}Cl_2NO \cdot HCl$ (274.62): C, 43.74; H, 6.61; N, 5.10. Found: C, 43.71; H, 6.53; N, 4.85.

The mother liquors were combined and evaporated to dryness. Recrystallization of the residue from acetone gave 1,1-dichloro-3-[3(R)-vinyl-4(S)-piperidinyl]propan-2(R)-ol hydrochloride, m.p. 165°-167°, $[\alpha]_D^{25}$ + 30.7° (c 1.00, methanol).

Analysis Calcd. for $C_{10}H_{17}Cl_2NO \cdot HCl$ (274.62): C, 43.74; H, 6.61; N, 5.10. Found: C, 44.01; H, 6.86; N, 4.78.

EXAMPLE 9

Preparation of
1,1-dichloro-3-[3(R)-ethyl-4(S)-piperidinyl]propan-2(S)-ol hydrochloride and
1,1-dichloro-3-[3(R)-ethyl-4(S)-piperidinyl]propan-2(R)-ol hydrochloride To a solution containing 6.35 ml. of methylene chloride in 120 ml. of anhydrous tetrahydrofuran cooled to −70° there was added over a period of 2 hours 90 mmoles of n-butyllithium in 55.5 ml. of hexane under an atmosphere of dry nitrogen. The mixture was stirred at the same temperature for 30 minutes and then followed by the dropwise addition of 5.8 g. (22.4 mmoles) of 2-[1-benzoyl-3(R)-ethyl-4(S)-piperidinyl]acetaldehyde in 60 ml. of anhydrous tetrahydrofuran. After 30 minutes, the reaction was quenched by the addition of 30 ml. of water. The mixture was allowed to warm up to room temperature and was subsequently extracted three times with ether. The combined ether extracts were extracted with 300 ml. of 10 percent aqueous hydrochloric acid. The acidic solution was washed twice with each 100 ml. of ether and evaporated to complete dryness. The residue was dissolved in the minimal amount of hot ethanol. Upon standing, there was obtained 1.1 g. of 1,1-dichloro-3-[3(R)-ethyl-4(S)-piperidinyl]propan-2 (S)-ol hydrochloride, mp 239-240°, $[\alpha]^{25}$ D −28.6° (c 1.005, methanol), after recrystallization from ethanol.

The mother liquors were combined and evaporated to dryness. Recrystallization of the residue from acetone gave 1,1-dichloro-3-[3(R)-ethyl-4(S)-piperidinyl]propan-2(R)-ol hydrochloride, mp 172°-173°, $[\alpha]^{25}$ D +25.2° (c 1.00, methanol).

EXAMPLE 10

Preparation of epimeric, racemic 4,5-erythro-5-ethylquinuclidine-2$\xi$-carboxaldehydes a. To a solution containing 2.77 g. of racemic 1,1-dichloro-3-[3(R)-ethyl-4(S)-piperidinyl]propan-2(S)-ol HCl in 20 ml. of methanol was added a solution containing 1.68 g. of potassium hydroxide in 15.8 ml. of methanol. The mixture was stirred at room temperature for 55 hours. The precipitate formed in the reaction was removed by filtration, and the filtrate was evaporated to dryness. The residue was treated with 200 ml. of ether, and the insoluble part was removed by filtration. The filtrate was evaporated to dryness to yield and oily mixture of epimeric, racemic 4,5-erythro-5-ethylquinuclidine-2$\xi$-carboxaldehydes.

b. The methanolic solution containing crude aldehyde prepared as above from 5.45 g. of racemic 1,1-dichloro-3-[3(R)-ethyl-4(S)-piperidinyl]propan-2(S)-ol hydrochloride was evaporated to dryness under reduced pressure at a temperature below 30°. The residue was dissolved in 300 ml. of ether, insoluble material was removed by filtration, and evaporation of the filtrate gave 4.12 g. of oily residue. A solution of the residue in 100 ml. of ether was added to a solution containing 2.5 g. of sodium bisulfite in 8 ml. of water. The solvents were removed under reduced pressure, and the residue was dissolved in 10 ml. of water. Addition of ethanol followed by the addition of ether precipitated 3.4 g. of solid addition product. This product was added to 50 ml. of a saturated aqueous sodium carbonate and heated at 40°. After all material had dissolved, the solution was kept at 40° for another 5 minutes. The mixture was cooled and extracted three times with ether. The combined ether extracts were dried over potassium carbonate and evaporated to dryness under reduced pressure to give 950 mg. of liquid aldehyde. Distillation in a short path distillation apparatus at 60°-85° (oil bath temperature) under a pressure of 0.4 mmHg. gave 648 mg. of analytically pure mixture of epimeric, racemic, 4,5-erythro-5-ethylquinuclidine-2$\xi$-carboxaldehydes.

Analysis Calcd. for $C_{10}H_{17}NO$ (167.24): C, 71.81; H, 10.25; N, 8.38. Found: C, 71.91; H, 10.02; N, 8.58.

c. A solution containing 1.39 g. of racemic 1,1-dichloro-3-[3(R)ethyl-4(S)-piperidinyl]propan-2(R)-ol HCl in 25 ml. of water was combined with 150 ml. of benzene. The stirred mixture was cooled in an ice bath and 8.56 ml. of a 1.75N potassium hydroxide solution was added slowly. Stirring at room temperature was continued under an atmosphere of nitrogen for 20 hours. The aqueous layer was separated and extracted with benzene. The combined organic layer was dried over sodium sulfate and evaporated under reduced pressure at approximately 30°. The residue was distilled in a short path distillation apparatus at 60°-85° (oil bath temperature) and 0.3 mmHg. to give 600 mg. (72 percent) of a mixture of epimeric, racemic 4,5-erythro-5-ethylquinuclidine-2$\xi$-carboxaldehydes.

d. To a solution of 400 mg. of racemic, epimeric cis 1,1-dichloro-3-(3-ethyl-4-piperidinyl)propan-2$\xi$-ols in 50 ml. of methanol was added 5 g. of Amberlite anion exchange resin IRA-401 (OH). The mixture was stirred at room temperature overnight. The resin was removed by filtration. The filtrate was concentrated to near dryness under reduced pressure and the residue was treated with benzene. The benzene solution was dried over MgSO₄ and evaporated to dryness under reduced pressure to give epimeric, racemic 4,5-erythro-5-ethylquinuclidine-2$\xi$-carboxaldehydes.

EXAMPLE 11

Preparation of epimeric
5(R)-ethyl-4(S)-quinuclidine-2$\xi$-carboxaldehydes a. A solution containing 1.14 g. of 1,1-dichloro-3-[3(R)-ethyl-4(S)-piperidinyl]propan-2(S)-ol hydrochloride in 20 ml. of water was combined with 450 ml. of benzene. The stirred mixture was cooled in an ice bath and 7.4 ml. of a 1.68N potassium hydroxide solution was added slowly. Stirring at room temperature was continued under an atmosphere of nitrogen for 20 hours. The aqueous layer was separated and extracted with benzene. The combined organic layer was dried over sodium sulfate and evaporated under reduced pressure at 30°. The residue on evaporative bulb-to-bulb distillation at 80° and 0.1 mmHg yielded 283 mg. of liquid epimeric 5(R)-ethyl-4(S)-quinuclidine-2$\xi$-carboxaldehydes, $[\alpha]^{25}$ D +102.61 (c 1.1383, methanol).

Analysis Calcd. for $C_{10}H_{17}NO$ (167.24): C, 71,81; H, 10.25; N, 8.38. Found: C, 71.75; H, 9.97; N, 8.44.

b. Utilizing the procedure above, a mixture of 1.94 g. of 1,1-dichloro-3-[3(R)-ethyl-4(S)-piperidinyl]propan-2(S)-ol hydrochloride and 1,1-dichloro-3-[3(R)-ethyl-4(S)-piperidinyl]propan-2(R)-ol hydrochloride gave after evaporative bulb-to-bulb distillation at 80° and 0.3 mmHg 538 mg. of epimeric 5(R)-ethyl-4(S)-quinuclidine-2$\xi$-carboxaldehydes.

EXAMPLE 12

Preparation of epimeric
5(S)-ethyl-4(R)-quinuclidine-2$\xi$-carboxaldehydes

A solution containing 1.34 g. of 1,1-dichloro-3-[3(S)-ethyl-4(R)-piperidinyl]propan-2(S)-ol hydrochloride in 10 ml. of water was combined with 150 ml. of benzene. The stirred mixture was cooled in an ice-bath and 8.7 ml. of a 1.68N potassium hydroxide solution was added slowly. Stirring at room temperature was continued under an atmosphere of nitrogen for 20 hours. The aqueous layer was separated and extracted with benzene. The combined organic layer was dried over sodium sulfate and evaporated under reduced pressure at 30°. The residue on evaporative bulb-to-bulb distillation at 90° and 0.1 mmHg yielded 500 mg. of liquid epimeric 5(S)-ethyl-4(R)-quinuclidine-2$\xi$-carboxaldehydes, $[\alpha]^{25}$ D −85.56° (c 1.0682, methanol).

Analysis Calcd. for $C_{10}H_{17}NO$ (167.24): C, 71.81; H, 10.25; N, 8.38. Found: C, 71.55; H, 10.29; N, 8.65.

EXAMPLE 13

Preparation of epimeric
5(R)-vinyl-4(S)-quinuclidine-2$\xi$-carboxaldehydes

A solution containing 2.36 g. of a mixture of 1,1-dichloro-3-[3(R)-vinyl-4(S)-piperidinyl]propan-2(S)-ol hydrochloride and 1,1-dichloro-3-[3(R)-vinyl-4(S)-piperidinyl]propan-2(R)-ol hydrochloride in 35 ml. of water was combined with 850 ml. of benzene. The stirred mixture was cooled in an ice bath and 15.4 ml. of 1.68N potassium hydroxide solution was added slowly under a nitrogen atmosphere. Stirring at room temperature was continued for 16 hours. The aqueous layer was separated and extracted with benzene. The combined organic layers were washed with water, dried over sodium suflate and evaporated under reduced pressure at 30°. The residue on evaporative bulb-to-bulb distillation at 60° and 0.05 mmHg. yielded 767 mg. of liquid epimeric 5(R)-vinyl-4(S)-quinuclidine-2$\xi$-carboxaldehydes, $[\alpha]^{25}$ D +154.85° (c 0.8957, chloroform).

EXAMPLE 14

Preparation of epimeric, racemic
4,5-erythro-5-ethylquinuclidine-2$\xi$-carboxylic acid ethyl esters a. To a solution containing 8.3 g. of racemic 1,1-dichloro-3-[3(R)-ethyl-4(S)-piperidinyl]propan-2(S)-ol hydrochloride in 600 ml. of methanol cooled to 0° was added dropwise with stirring a solution of 5.04 g. of potassium hydroxide in 23.4 ml. of methanol. After completed addition, the temperature of the mixture was allowed to rise to room temperature and stirring was continued overnight. Insoluble material was removed by filtration, and the solution was added to a mixture of 11.7 g. of silver nitrate and 4.8 g. of sodium hydroxide in 200 ml. of water. The reaction mixture, after stirring for 3 hours at room temperature, was filtered through Celite-Filter Aid and the filtrate was saturated with hydrogen sulfide. The precipitate was removed by filtration through Celite-Filter Aid and the filtrate was evaporated to dryness. The residue was treated with 500 ml. of ethanol, and the mixture was refluxed for 3 hours. After filtering through Celite-Filter Aid, the filtrate containing a mixture of epimeric, racemic 4,5-erythro-5-ethylquinuclidine-2$\xi$-carboxylic acids was saturated with anhydrous hydrogen chloride and refluxed overnight. The precipitate was removed by filtration, and the filtrate was evaporated to dryness. The yellow oil obtained was treated with 300 ml. of a saturated aqueous solution of sodium carbonate and extracted five times with ether. The combined ether extract was dried over sodium sulfate and evaporated to dryness under reduced pressure. The residue was distilled in a short path distillation apparatus at 70°–75°C. (oil bath temperature) under a pressure of 0.3 mmHg. to give 3.81 g. (60 percent) of a liquid mixture of epimeric, racemic 4,5-erythro-5-ethylquinuclidine-2$\xi$-carboxylic acid ethyl esters.

Gas chromatography on a column of 4 percent PEG 4000 MS on Gaschrom Z at 150° showed the material to consist of two isomers in a 1:1 ratio with retention times of $t_o = 8.5$ min. and $t_o = 9.4$ min. A separation of the two isomers was achieved by preparative gas chromatography. In the mass spectrum, both isomers showed a low resolution molecular ion peak at m/e 211 and a base peak at m/e 138.

b. To a solution of 5 ml. of methylene chloride in 70 ml. of anhydrous tetrahydrofuran cooled to −70° was added during 1 hour 35 ml. of a 1.66M solution of n-butyllithium in hexane under an atmosphere of dry nitrogen. The mixture was stirred at the same temperature for 20 minutes, which was followed by the dropwise addition of 6.8 g. of racemic 2-[1-benzoyl-3(R)-ethyl-4(S)-piperidinyl]acetaldehyde in 30 ml. of anhydrous tetrahydrofuran. After 30 minutes, the reaction was quenched by the addition of 30 ml. of water. The mixture was allowed to warm up to room temperature and was subsequently extracted three times with ether. The combined ether extracts were washed with water, dried over sodium sulfate and evaporated to dryness.

The product (4 g.), a mixture of racemic, epimeric 1,1-dichloro-3-[3(R)-ethyl-4(S)-piperidinyl]propan-2ξ-ols, was dissolved in 400 ml. of methanol. A solution of 1.8 g. of potassium hydroxide in 45 ml. of methanol was added and stirring was continued for 50 hours at room temperature. Then, the solution containing a mixture of racemic, epimeric 4,5-erythro-5-ethylquinuclidine-2ξ-carboxaldehydes was combined with a mixture of 2.56 g. of sodium hydroxide and 5.44 g. of silver nitrate in 60 ml. of water. The reaction mixture, after being stirred for 3 hours at room temperature, was filtered through Celite-Filter Aid, and the filtrate was evaporated to dryness. Complete dryness was ensured by the addition of an ethanol-benzene solvent mixture to the residue followed by removal of the solvents under reduced pressure. The procedure was repeated several times. The residue was extracted repeatedly with hot ethanol. The combined extracts were evaporated to dryness and the residue containing a mixture of epimeric, racemic 4,5-erythro-5-ethylquinuclidine-2ξ-carboxylic acids, was esterified with 4 percent ethanolic hydrogen chloride to give, after usual work-up and distillation under reduced pressure, 1.8 g. of a mixture of epimeric, racemic 4,5-erythro- 5-ethylquinuclidine-2ξ-carboxylic acid ethyl esters.

EXAMPLE 15

Preparation of epimeric, racemic 4,5-erythro-5-ethylquinuclidine-2ξ-carboxylic acid methyl esters A mixture of epimeric, racemic 4,5-erythro-5-ethylquinuclidine-2ξ-carboxylic acids, obtained from 5.53 g. of racemic 1,1-dichloro-3-[3(R)-ethyl-4(S)-piperidinyl]propan-2(S)-ol HCl by the reaction sequence outlined previously in Example 10 (a), was dissolved in 350 ml. of methanol. Concentrated sulfuric acid (5 ml.) was added, and the mixture was refluxed overnight. After the addition of another 2 ml. of concentrated sulfuric acid, refluxing was continued for another 15 hours. The volume was reduced to approximately 30 ml. by evaporation under reduced pressure. The resulting residue was rendered alkaline with a saturated aqueous solution of sodium carbonate and diluted with dichloromethane. The insoluble material was removed by filtration and dissolved in the minimal amount of water. The aqueous phase was extracted three times with dichloromethane and the extracts were combined with the filtrate. The combined organic layer was dried over potassium carbonate and evaporated under reduced pressure. The residue, on distillation, gave 2.33 g. (59 percent) of a liquid mixture of epimeric, racemic 4,5-erythro-5-ethylquinuclidine-2ξ-carboxylic acid methyl esters, b.p. 84°–85°/0.35 mmHg.

EXAMPLE 16

Preparation of epimeric 5(R)-ethyl-4(S)-quinuclidine-2ξ-carboxylic acid ethyl esters To a solution containing 3.2 g. of a mixture of 1,1-dichloro-3-[3(R)-ethyl-4(S)-piperidinyl]propan-2(S)-ol hydrochloride and 1,1-dichloro-3 [3(R)-ethyl-4(S)-piperidinyl]propan-2(R)-ol hydrochloride in 350 ml. of methanol cooled to 0° was added dropwise with stirring a solution of 1.95 g. of potassium hydroxide in 21.7 ml. of methanol. Stirring was continued at room temperature overnight. The insoluble material was removed by filtration, and the solution was added to a mixture of 3.96 g. of silver nitrate and 1.85 g. of sodium hydroxide in 35 ml. of water. The reaction mixture, after stirring for 4 hours at room temperature, was filtered through Celite-Filter Aid and the filtrate was evaporated to dryness. The residue was extracted with 200 ml. of boiling ethanol. The extract containing a mixture of epimeric 5(R)-ethyl-4(S)-quinuclidine-2ξ-carboxylic acids was evaporated to complete dryness. The residue was dissolved in 4 percent ethanolic hydrogen chloride and the solution was refluxed overnight. This procedure was repeated once more. After removal of the precipitate by filtration, the filtrate was evaporated to dryness. The residue was rendered alkaline with a saturated aqueous solution of potassium carbonate and extracted three times with ether. The combined ether extracts were dried over potassium carbonate and evaporated to dryness under reduced pressure. Evaporative bulb-to-bulb distillation at 95°–97° and 0.05 mmHg of the crude product yielded 1 g. of liquid epimeric 5(R)-ethyl-4(S)-quinuclidine-2ξ-carboxylic acid ethyl ester, $[\alpha]^{25}$ D +77.32° (c 1.0489, methanol).

Analysis Calcd. for $C_{12}H_{21}NO_2$ (211.30): C, 68.21; H, 10.02; N, 6.63. Found: C, 68.47; H, 10.25; N, 6.74.

EXAMPLE 17

Preparation of epimeric, racemic 4,5-erythro-5-ethylquinuclidine-2ξ-carboxylic acids hydrochlorides A solution containing 2.15 g. of a mixture of epimeric, racemiic 4,5-erythro-5-ethylquinuclidine-2ξ-carboxylic acid ethyl esters in 100 ml. of 1N hydrochloric acid was left standing at room temperature for 10 days. The solution was washed with ether and evaporated to dryness under reduced pressure. Complete dryness was ensured by repeatedly adding toluene to the residue and removing the solvent under reduced pressure. The residue was crystallized from ethanol-ether to give 429 mg. of a mixture of epimeric, racemic 4,5-erythro-5-ethylquinuclidine-2ξ-carboxylic acids hydrochlorides, m.p. 239°–242°.

Analysis Calcd. for $C_{10}H_{17}NO_2 \cdot HCl$ (219.72): C, 54.67; H, 8.26; N, 6.38. Found: C, 54.80; H 8.35; N, 6.24.

The concentrated mother liquor was treated again with 1N hydrochloric acid and yielded an additional 353 mg. of a mixture of epimeric, racemic 4,5-erythro-5-ethylquinuclidine-2ξ-carboxylic acid hydrochlorides.

EXAMPLE 18

Preparation of epimeric 5(R)-vinyl-4(S)-quinuclidine-2ξ-carboxylic acid ethyl esters Utilizing the conditions described in Example 8, 6.48 g. of 2-[1-benzoyl-3(R)-vinyl-4(S)-piperidinyl]acetaldehyde was reacted with dichloromethyllithium prepared from 3.7 ml. of methylene chloride and 55 mmoles of n-butyllithium. The resulting product (4.1 g.), a mixture of epimeric 1,1-dichloro-3-[3(R)-vinyl-4(S)-piperidinyl]propan-2ξ-ols, was dissolved in 400 ml. of methanol. A solution containing 1.9 g. of potassium hydroxide in 20 ml. of methanol was added and stirring was continued for 50 hours at room temperature. The solution containing a mixture of epimeric 5(R)-vinyl-4(S)-quinuclidine-2ξ-carboxaldehydes was combined with a mixture of 2.56 g. of sodium hydroxide and 5.78 g. of silver nitrate in 40 ml. of water. The resulting reaction mixture, after being stirred for 3 hours at room temperature, was filtered through Celite-Filter Aid, and the filtrate was evaporated to dryness. Complete dryness was ensured by the addition of an ethanol-benzene solvent mixture to the residue followed by removal of the solvents under reduced pressure. The procedure was repeated several times. The residue was extracted repeatedly with hot ethanol. The combined extract was evaporated to dryness and the residue containing a mixture of epimeric 5(R)-vinyl-4(S)-quinuclidine-2$\xi$-carboxylic acids was partially dissolved in 100 ml. of 8 percent ethanolic hydrogen chloride. The reaction mixture was stirred at room temperature for 3 days and then evaporated to dryness. The residue was treated again with 100 ml. of 5 percent ethanolic hydrogen chloride for 15 hours. The solvent was removed under reduced pressure, and the residue was combined with 100 ml. of a saturated aqueous solution of potassium carbonate. The mixture was extracted three times with ether. The combined ether extracts were dried over sodium sulfate and evaporated to dryness under reduced pressure. The residue was distilled in a short path distillation apparatus at 77° (oil bath temperature) under a pressure of 0.15 mmHg. to give 1.88 g. (36 percent) of liquid epimeric 5(R)-vinyl-4(S)-quinuclidine-2$\xi$-carboxylic acid ethyl esters; $[\alpha]_D^{25}$ +82.2° (c 1.1, 95% ethanol).

EXAMPLE 19

Preparation of epimeric
5(R)-vinyl-4(S)-quinuclidine-2$\xi$-carboxylic acids

A suspension of 310 mg. of epimeric 5(R)-vinyl-4(S)-quinuclidine-2$\xi$-carboxylic acid ethyl esters in 10 ml. of water was left standing at room temperature. After 10 days, a clear solution was obtained. The water was evaporated under reduced pressure, and the residue was sublimed at 165° under a pressure of 0.15 mmHg. to give 210 mg. of very hygroscopic crystalline epimeric 5(R)-vinyl-4(S)-quinuclidine-2$\xi$-carboxylic acids; $[\alpha]_D^{25}$ +78.4° (c 0.72, CHCl$_3$), $[\alpha]_D^{25}$ +93.2° (c 0.87, 1N NaOH) measured immediately and $[\alpha]_D^{25}$ +80.8° (c 0.87, 1N NaOH) after heating the solution at 100° for 16 hours.

EXAMPLE 20

Preparation of racemic dihydroquininone and racemic dihydroquinidinone a. To a solution containing 488 mg. of 4-bromo-6-methoxyquinoline in 20 ml. of anhydrous ether was added under nitrogen at −50° 0.45 ml. of a 2.25M solution of butyllithium in hexane. The suspension containing 6-methoxy-4-quinolyllithium was stirred at this temperature for another 15 minutes and then a solution of 433 mg. of a mixture of epimeric, racemic 4,5-erythro-5-ethyl-quinuclidine-2$\xi$-carboxylic acid ethyl esters in 20 ml. of anhydrous ether was added over a period of 20 minutes. After stirring at −50° for another 1.5 hours, the mixture was warmed to room temperature and hydrolyzed by the addition of water. The aqueous layer was separated and extracted three times with ether. The combined organic solution was dried over sodium sulfate and evaporated to dryness. The crude product was chromatographed on silica gel preparative plates with ether as solvent. The plates were run three times. Elution with methanol gave 100 mg. of a yellow oil which on further treatment gave 50 mg. of a crystalline mixture of racemic dihydroquininone and racemic dihydroquinidinone, m.p. 86°–90°.

b. To 5 ml. of anhydrous ether was added 0.67 ml. of 1.66M solution of butyllithium in hexane. The resulting solution was cooled to −70° and with stirring and under a nitrogen atmosphere, 119 mg. of 4-bromo-6-methoxyquinoline dissolved in 5 ml. of ether was added. The suspension containing 6-methoxy-4-quinolyllithium was combined with 56 mg. of 1,4-diazabicyclo[2.2.2]octane dissolved in 5 ml. of anhydrous ether and the mixture was stirred at −70° for 2 hours. Thereafter, a solution of 126 mg. of a mixture of epimeric, racemic 4,5-erythro-5-ethylquinuclidine-2$\xi$-carboxylic acid ethyl esters in 5 ml. of anhydrous ether was added. After stirring at −70° for 30 minutes, the mixture was quenched with water and allowed to warm up to room temperature. The aqueous layer was separated and extracted with ether. The combined organic solution was dried over sodium sulfate and evaporated to dryness to give 184 mg. of an oil containing racemic dihydroquininone and racemic dihydroquinidinone.

Utilizing the procedure described above, there can be obtained:

a. from 7-chloro-4-quinolyllithium, a mixture of racemic 7'-chlorodihydrocinchonidinone and racemic 7'-chlorodihydrocinchoninone, m.p. 124°–127°;
b. from 6-methyl-4-quinolyllithium, a mixture of racemic 6'-methyldihydrocinchonidinone and racemic 6'-methyldihydrocinchoninone, m.p. 105°–108°;
c. from 6-chloro-4-quinolyllithium, a mixture of racemic 6'-chlorodihydrocinchonidinone and racemic 6'-chlorodihydrocinchoninone, m.p. 104°–107°;
d. from 7-methoxy-4-quinolyllithium, a mixture of racemic 7'-methoxydihydrocinchonidinone and racemic 7'-methoxydihydrocinchoninone, m.p. 111°–117°; and the like.

EXAMPLE 21

Preparation of racemic dihydroquinine and racemic dihydroquinidine from a mixture of racemic dihydroquininone and racemic dihydroquinidinone To a solution of 5.06 g. of a crystalline mixture of racemic dihydroquininone and dihydroquinidinone in 500 ml. of dry benzene was added dropwise 12.5 ml. of a 25 percent solution of diisobutylaluminum hydride in toluene with stirring under an atmosphere of dry nitrogen. After approximately 30 minutes, the reaction was quenched by the addition of 2 ml. of methanol-water (1:1). The precipitated alumina was separated by filtration and washed thoroughly with methanol. The residue of the methanol washings (3.87 g.) was crystallized from acetone yielding 3.14 g. (61 percent) of racemic dihydroquinine monohydrate in three crops. The residue of the benzene solution (1.54 g.) was crystallized from a concentrated solution in ethanol yielding 579 mg. (11 percent) of racemic dihydroquinidine in four crops. After purification on preparative tlc (chloroform-triethylamine-methanol, 85:10:5) more d,l-dihydroquinidine and d,l-dihydroquinine could be crystallized from ethanol and acetone, respectively.

Utilizing the procedure described above:

a. from a mixture of racemic 7'-chlorodihydrocinchonidinone and racemic 7'-chlorodihydrocinchoninone, there can be obtained racemic 7'-chlorodihydrocinchonidine, m.p. 192°–193°, and racemic 7'-chlorodihydrocinchonine, m.p. 251°–253° dec.;

b. from a mixture of racemic 7'-methoxydihydrocinchonidinone and racemic 7'-methoxydihydrocinchoninone, there can be obtained racemic 7'-methoxydihydrocinchonidine, m.p. 160°, and racemic 7'-methoxydihydrocinchonine, m.p. 217°–219°;

c. from a mixture of racemic 6'-methyldihydrocinchonidinone and racemic 6'-methyldihydrocinchoninone, there can be obtained, racemic 6'-methyldihydrocinchonidine, m.p. 216°–218°, and racemic 6'-methyldihydrocinchonine, m.p. 153.5° – 155°;

d. from a mixture of racemic 6'-chlorodihydrocinchonidinone and racemic 6'-chlorodihydrocinchoninone, there can be obtained racemic 6'-chlorodihydrocinchonidine, m.p. 100°–102°, and racemic 6'-chlorodihydrocinchonine, m.p. 172.5° – 173.5°.

EXAMPLE 22

Preparation of Quinine and Quinidine

To 100 ml. of anhydrous ether there was added 14.5 ml. of a 1.45M solution of n-butyllithium in hexane. The resulting solution was cooled to −70° and with stirring a solution of 4.76 g. of 4-bromo-6-methoxyquinoline in 100 ml. of anhydrous ether was added under an atmosphere of dry nitrogen. The yellow suspension of 6-methoxy-4-quinolyllithium in ether which immediately formed was stirred at −70° for 2 hours. A solution of 2.1 g. of epimeric 5(R-vinyl-4(S)-quinuclidine-2ξ-carboxylic acid ethyl esters in 100 ml. of anhydrous ether was added, and after 30 mins., the reaction was quenched by the addition of water and allowed to warm up to room temperature. The ethereal solution was washed with water, dried over sodium sulfate and evaporated to dryness under reduced pressure to yield 5.08 g. of an oil which contained a mixture of quininone and quinidinone. To a cooled solution of 4.74 g. of the above material in 100 ml. of anhydrous benzene, there was slowly added 13 ml. of a 25 percent solution of diisobutylaluminum hydride in toluene under an atmosphere of dry nitrogen. The reaction was quenched after 1 hour by the addition of 20 ml. of water-methanol (1:1) with vigorous stirring. The precipitate which formed was collected by filtration and washed thoroughly with methanol. The filtrate was dried over anhydrous sodium sulfate and evaporated to dryness. A solution of the residue in chloroform was washed successively with 1N sodium hydroxide and water, dried over anhydrous sodium sulfate and evaporated to dryness. The product (4.1 g.) was chromatographed on 150 g. of neutral alumina (Woelm, activity I) with ethyl acetate-benzene (1:1) (500 ml.), ethyl acetate (800 ml.) and methanol (400 ml.) as eluent. Evaporation of the methanol fraction gave 2.5 g. of product which was chromatographed on silica gel preparative plates (20 × 20 × 0.2 cm.) with chloroform-triethylamine-methanol (85:10:5) as the solvent mixture. Elution of the lowest of three major bands with chloroform-methanol (1:1) gave 289 mg. of a yellow oil which was dissolved in ethanol, and on treatment with 44 mg. of d-tartaric acid in ethanol yielded the crystalline, neutral tartrate of quinine, m.p. 214°–215°, $[\alpha]_D^{25}$ −149° (c, 0.985, MeOH). The compound showed ir-spectrum and tlc $R_f$-value identical with those of an authentic sample. The melting point was not depressed on admixture with an authentic specimen. Elution of the middle band with methanol-chloroform (1:1) gave 311 mg. of quinidine, which after recrystallization from ethanol and drying at 80° under reduced pressure for 15 hours showed m.p. 170°–172°, $[\alpha]_D^{22}$ + 261° (c, 0.995, ethanol). The ir-spectrum and the tlc $R_f$-value were identical with those of authentic material. No depression of the melting point was observed on admixture with an authentic sample. The upper band, upon elution with methanol-chloroform (1:1) yielded 95 mg. of oily residue which was identical with an authentic mixture of epiquinine and epi-quinidine.

Utilizing the reaction conditions described above:

a. from 7-chloro-4-quinolyllithium, there can be obtained, 7'-chlorocinchonidine, m.p. 177–179°, and 7'-chlorocinchonine, m.p. 245°–246°;

b. from 6,8-dichloro-4-quinolyllithium, there can be obtained, 6',8'-dichlorocinchonidine, m.p. 105°–108°, and 6',8'-dichlorocinchonine dihydrochloride monohydrate, m.p. 250° dec.;

c. from 6-chloro-4-quinolyllithium, there can be obtained, 6'-chlorocinchonidine, m.p. 193°–194°, and 6'-chlorocinchonine, m.p. 154°–155°;

d. from 4-quinolyllithium, there can be obtained, cinchonidine and cinchonine.

EXAMPLE 23

Preparation of Quinine and Quinidine

To 30 ml. of anhydrous ether was added 2.74 ml. of a 1.62M solution of butyllithium in hexane. The resulting solution was cooled to −70°. With stirring under a nitrogen atmosphere, a solution of 1.08 g. of 4-bromo-6-methoxyquinoline in 30 ml. of anhydrous tetrahydrofuran was added. After stirring the mixture containing 6-methoxy-4-quinolyllithium for 30 minutes at −70°, a solution of 748 mg. of freshly distilled 5(R)-vinyl-4(S)-quinuclidine-2ξ-carboxaldehyde in 15 ml. of anhydrous ether was added over a period of 30 minutes. After the addition was completed, stirring was continued for two hours at 70°. The reaction mixture then was hydrolyzed by the addition of water and extracted several times with ether. The organic extract was washed with water, dried over anhydrous sodium sulfate and evaporated to dryness. The residue was chromatographed on Merck F-254 silica gel preparative plates with chloroform-triethylamine-methanol (85:10:5) as the solvent mixture. Elution of three separate bands and purification of the eluates yielded 215 mg. of quinidine [mp 172–173°; $[\alpha]_D^{25}$ +265.6° (c 1.07, 95 percent ethanol)], 220 mg. of the neutral d-tartrate of quinine [mp 211–212°; $[\alpha]_D^{25}$ −159.5° (c 1.00, methanol)], and 330 mg. of a mixture of epi-quinine and epi-quinidine.

EXAMPLE 24

Preparation of racemic 6',8'-dichlorodihydrocinchonidine dihydrochloride and racemic 6',8'-dichlorodihydrocinchonine dihydrochloride a. To 500 ml. of anhydrous ether was added 38 ml. of 1.45M solution of butyllithium in hexane. The resulting solution was cooled to −68° and with stirring and under a nitrogen atmosphere 13.8 g. of 4-bromo-6,8-dichloroquinoline dissolved in 175 ml. of anhydrous tetrahydrofuran was added over a period of 30 minutes. Subsequently, a solution of 5.3 g. of a mixture of epimeric, racemic 4,5-erythro-5-ethylquinuclidine-2ξ-carboxylic acid ethyl esters in 250 ml. of anhydrous ether was added to the 6,8-dichloro-4-quinolyllithium, thus prepared, and stirring was continued for one hour at −70°. The reaction was then quenched by the addition of water and allowed to warm up to room temperature. The organic solution was washed with water, dried over sodium sulfate and evaporated to dryness under reduced pressure to yield 19.0 g. of an oily residue containing a mixture of racemic 6',8'-dichlorodihydrocinchonidinone and racemic 6',8'-dichlorodihydrocinchoninone. This material was dissolved in 250 ml. of anhydrous benzene and cooled. To the cooled solution there was added over a period of 15 minutes 17 ml. of a 25% solution of diisobutylaluminum hydride in toluene under an atmosphere of dry nitrogen. The reaction mixture was stirred for one hour at room temperature and then quenched by the addition of 20 ml. of water-methanol (1:1). The precipitate was collected by filtration and washed thoroughly with methanol. A solution of the residue in chloroform was washed with 1N sodium hydroxide and water. The organic solutions were combined, dried over sodium sulfate and evaporated to dryness under reduced pressure. The resulting product (14.1 g.) was chromatographed on 500 g. of neutral alumina (Woelm, activity I) with ethyl acetate (1.8 l.) followed by methanol (2.2 l.) as the eluent. Evaporation of the methanol fractions yielded 5.27 g. of product which together with 6.9 g. of material obtained previously was chromatographed on 700 g. of silica gel (Silica Gel 0.05-0.2 mm.; i.d. of column = 55 mm.). Fractions of 250 ml. each were collected. After 25 fractions with chloroform-triethylamine (97:3) as the liquid phase, the composition of the eluent was changed to 96:4. Fractions 29–40 were combined, evaporated to dryness and the residue was dissolved in dichloromethane. The organic solution was washed twice with water, dried over sodium sulfate and evaporated to dryness under reduced pressure. Crystallization of the residue (1.79 g.) from a mixture of benzene-hexane (1:2) gave 1.3 g. of crystalline, racemic 6',8'-dichlorodihydrocinchonine. Recrystallization from benzene-hexane (1:1) and drying of the sample at 80° under reduced pressure to constant weight yielded racemic 6',8'-dichlorodihydrocinchonine, containing ⅓ mole of benzene: m.p. 172°–173°.

Analysis Calcd. for $C_{19}H_{22}Cl_2N_2O \cdot \frac{1}{3} C_6H_6$ (391.35): C, 64.45; H, 6.18; N, 7.15; Cl, 18.12. Found: C, 64.63; H, 6.42; N, 7.28; Cl, 18.46.

The dihydrochloride salt of 6',8'-dichlorodihydrocinchonine was prepared by dissolving 1.05 g. of the free base in a minimal amount of ethanolic hydrogen chloride. Upon addition of ether to the solution, 1.0 g. of crystalline racemic 6',8'-dichlorodihydrocinchonine dihydrochloride precipitated, m.p. 210°–212°. Upon two recrystallizations from ethanol-ether the melting point was 214°–215° (dried for 100 minutes at 80° under reduced pressure).

Analysis Calcd. for $C_{19}H_{22}Cl_2N_2O \cdot 2HCl$ (438.22): C, 52.07; H, 5.52; N, 6.39; Cl, 32.36. Found: C, 52.14; H, 5.56; N, 6.42; Cl, 31.90.

Fractions 42–57 were combined and evaporated to dryness. The residue was dissolved in dichloromethane. The solution was washed twice with water, dried over sodium sulfate and evaporated to dryness under reduced pressure. The residue (1.56 g.) was dissolved in the minimal amount of ethanolic hydrogen chloride and upon addition of ether to the solution 1.15 g. of crystalline racemic 6',8'-dichlorodihydrocinchonidine dihydrochloride was precipitated. Recrystallization from methanol-ether yielded analytically pure racemic 6',8'-dichlorodihydrocinchonidine dihydrochloride, m.p. 226°–227°.

Analysis Calcd. for $C_{19}H_{22}Cl_2N_2O \cdot 2HCl$ (438.22): C, 52.07; H, 5.52; N, 6.39; Cl, 32.36. Found: C, 52.04; H, 5.63; N, 6.29; Cl, 32.17.

b. To 500 ml. of anhydrous ether was added 38 ml. of 1.45M solution of butyllithium in hexane. The resulting solution was cooled to −70° and with stirring and under a nitrogen atmosphere, 13.8 g. of 4-bromo-6,8-dichloroquinoline dissolved in 200 ml. of anhydrous tetrahydrofuran was added. Stirring of the solution of 6,8-dichloro-4-quinolyllithium was continued at −70° for another 10 minutes, followed by the addition of 5.6 g. of anhydrous tetramethylethylenediamine dissolved in 250 -quinuclidine- of anhydrous ether. After additional stirring for 15 minutes, there was added 5.8 g. of a mixture of epimeric, racemic 4,5-erythro-5-ethylquinuclidine-2ξ-carboxylic acid ethyl ester dissolved in 250 ml. of anhydrous ether. The mixture was stirred at −70° for one hour, then quenched by the addition of water and allowed to warm up to room temperature. The organic solution was washed with water, dried over sodium sulfate and evaporated to dryness under reduced pressure to yield 17.5 g. of an oily residue containing a mixture of racemic 6',8'-dichlorodihydrocinchonidinone and racemic 6',8'-dichlorodihydrocinchoninone. Subsequent conversion to racemic 6',8'-dichlorodihydrocinchonidine dihydrochloride and 6',8'-dichlorodihydrocinchonine was carried out as described in (a) above.

Utilizing the reaction conditions described above:

a. from 6,7-dimethoxy-4-quinolyllithium there can be obtained, racemic 6,7-dimethoxydihydrocinchonidine dihydrochloride, m.p. 208°–210° dec., and racemic 6',7'-dimethoxydihydrocinchonine dihydrochloride, m.p. 221°–225°.

b. from 6,7-methylenedioxy-4-quinolyllithium, there can be obtained racemic 6',7'-methylenedioxydihydrocinchonidine, m.p. 232°–233°, and racemic 6',7'-methylenedioxydihydrocinchonine, m.p. 234°–235°.

EXAMPLE 25

Preparation of racemic dihydroquinine and racemic dihydroquinidine

To 30 ml. of anhydrous ether was added 2.22 ml. of a 2.25M solution of butyllithium in hexane. The resulting solution was cooled to −68°C. and with stirring under a nitrogen atmosphere 1.19 g. of 4-bromo-6-methoxyquinoline was added. Immediately, a yellow suspension of 6-methoxy-4-quinolyllithium was formed. To this suspension was added within 5 minutes a solution of 1.42 g. of the crude mixture of epimeric, racemic 4,5-erythro-5-ethylquinuclidine-2ξ-carboxaldehydes in 30 ml. of anhydrous ether. After the addition was completed, stirring was continued for one hour at −65°C. The reaction mixture was then poured into an ice-water slurry and extracted with dichloromethane. The dichloromethane extract was washed with water, dried over anhydrous sodium sulfate and evaporated to dryness. The residue thus obtained was dissolved in dichloromethane and the solution was extracted twice with 2N hydrochloric acid. The acidic extract was washed with dichloromethane and then made alkaline by the addition of 6N aqueous sodium hydroxide. The free bases thus liberated were extracted into dichloromethane. The extract was washed with water, dried over anhydrous sodium sulfate and evaporated to dryness to give crude oily product. The crude product was chromatographed on Merck F-254 silica gel preparative plates with chloroform-triethylamine-methanol (85:10:5) mixture. Elution of two separated bands gave racemic dihydroquinidine, m.p. 153°–155° and racemic dihydroquinine, m.p. 171°–172°.

EXAMPLE 26

Preparation of racemic 6',7'-methylenedioxydihydrocinchonidine and racemic 6',7'-methylenedioxydihydrocinchonine To 250 ml. of anhydrous ether was added 19.3 ml. of a 1.45M solution of n-butyllithium in hexane. The resulting solution was cooled to −68°. Thereafter, there was added 6.55 g. of 4-bromo-6,7-methylenedioxyquinoline dissolved in 200 ml. of anhydrous tetrahydrofuran over a period of 30 minutes with stirring and under a nitrogen atmosphere to afford 6,7-methylenedioxy-4-quinolyllithium. Stirring of the mixture was continued at the same temperature for 30 minutes followed by the addition of a solution of 2.15 g. of a mixture of epimeric, racemic 4,5-erythro-5-ethylquinuclidine-2$\xi$-carboxaldehydes in 250 ml. of ether over a period of one hour. The reaction mixture was stirred at −70° under a nitrogen atmosphere overnight. After quenching with water, the mixture was allowed to warm to room temperature and subsequently was concentrated under reduced pressure. The residue was dissolved in ether. The ethereal solution was washed with water, dried over sodium sulfate and evaporated to dryness to give 6.54 g. of an oil. Chromatography on neutral alumina (Woelm, activity I) with ethyl acetate yielded 2.97 g. of a yellow solid. Subsequent elution with methanol yielded 3.37 g. of a brown oil. This was chromatographed on silica gel preparative plates (20 × 20 × 0.2 cm) with ethyl acetate-triethylamine (97:3) as the solvent mixture. The plates were developed three times. Elution of the lowest major band with methanol-chloroform and crystallization of the eluate (510 mg.) from acetone gave racemic 6',7'-methylenedioxy-dihydrocinchonidine, m.p. 232°–233°. Elution of the next higher band with methanolchloroform and crystallization of the eluate (597 mg.) from acetone gave racemic 6',7'-methylenedioxydihydrocinchonine, m.p. 234°–235°.

Analysis Calcd. for $C_{20}H_{24}N_2O_3$ (340.41): C, 70.56; H, 7.11; N, 8.23. Found: C, 70.25; H, 7.29; N, 8.05.

Utilizing the procedure described above:

a. from 6-methyl-4-quinolyllithium, there can be obtained racemic 6'-methyldihydrocinchonidine, m.p. 216°–218° and racemic 6'-methyldihydrocinchonine, m.p. 153.5° – 155°;
b. from 6-chloro-4-quinolyllithium, there can be obtained racemic 6'-chlorodihydrocinchonidine, m.p. 100°–102°, and racemic 6'-chlorodihydrocinchonine, m.p. 172.5° – 173.5°;
c. from 6,7-dimethoxy-4-quinolyllithium, there can be obtained racemic 6',7'-dimethoxydihydrocinchonidine dihydrochloride, m.p. 208°–210° dec., and racemic 6',7'-dimethoxydihydrocinchonine dihydrochloride, m.p. 221°–225°;
d. from 7-methoxy-4-quinolyllithium, there can be obtained racemic 7'-methoxydihydrocinchonidine, m.p. 160°, and racemic 7'-methoxydihydrocinchonine, m.p. 217°–219°;
e. from 6,8-dichloro-4-quinolyllithium, there can be obtained racemic 6',8'-dichlorodihydrocinchonidine dihydrochloride, m.p. 226°–227°, and racemic 6',8'-dichlorodihydrocinchonine dihydrochloride, m.p. 214°–215°.

EXAMPLE 27

Preparation of racemic 7'-chlorodihydrocinchonidine and racemic 7'-chlorodihydrocinchonine To a solution of 5.2 ml. of 1.62M butyllithium (in hexane) in 40 ml. of anhydrous ether and 10 ml. of anhydrous tetrahydrofuran was added at −70° under an atmosphere of nitrogen, 2.1 g. of 4-bromo-7-chloroquinoline dissolved in 30 ml. of anhydrous tetrahydrofuran. Stirring of the mixture containing 7-chloro-4-quinolyllithium was continued at the same temperature for 30 minutes followed by the addition of a solution of 1.4 g. of a mixture of epimeric, racemic 4,5-erythro-5-quinuclidine-12$\xi$-carboxaldehydes in 20 ml. of anhydrous ether. The reaction mixture was stirred at −70° for 2 hours. After quenching with water, the mixture was allowed to warm to room temperature. The aqueous layer was separated and extracted twice with ether. The combined organic extract was dried over sodium sulfate and evaporated to dryness under reduced pressure. The residue was chromatographed on 300 g. of silica gel (Merck 70-325) with chloroform-triethylamine as the liquid phase to afford racemic 7'-chlorodihydrocinchonidine, mp 188°–190° after recrystallization from acetone (mixture mp with an authentic sample 188°–190°), and racemic 7'-chlorodihydrocinchonine, mp 251°–252° after recrystallization from ethanol (mixture mp with an authentic sample 251°–252°).

EXAMPLE 28

Preparation of Dihydroquinine and Dihydroquinidine

To 20 ml. of anhydrous ether was added 1.98 ml. of a 1.62M solution of butyllithium in hexane. The resulting solution was cooled to −70° and with stirring under a nitrogen atmosphere a solution of 760 mg. of 4-bromo-6-methoxyquinoline in 20 ml. of anhydrous tetrahydrofuran was added. After stirring the mixture containing 6-methoxy-4-quinolyllithium for 30 minutes at −70°, a solution of 538 mg. of freshly distilled 5(R)-ethyl-4(S)-quinuclidine-2$\xi$-carboxaldehyde in 10 ml. of anhydrous ether was added during 15 minutes. After completion of the addition, stirring was continued for two hours at −70°. The reaction mixture then was hydrolyzed by the addition of water, allowed to warm up to room temperature and diluted with an equal volume of ether. The aqueous layer was separated and extracted three times with 15 ml. of ether each. The combined organic extract was dried over sodium sulfate and evaporated to dryness. The residue was chromatographed on silica gel plates (Merck F-254) with chloroform-triethylamine-methanol (85:10:5) as the solvent mixture. Elution of the lowest of the major bands with chloroform-methanol (1:1) gave 138 mg. of dihydroquinine, mp 169°–170° after recrystallization from chloroform-ether, $[\alpha]^{25}$ D −144.5° (c 0.935, 95 percent ethanol). The melting point was not depressed on admixture with a natural sample. Elution of the next higher band with chloroform-methanol (1:1) gave 210 mg. of an oil which was dissolved in ethanol. Upon standing, crystalline dihydroquinidine separated, mp 169°–170° (mixed mp with natural material 169°–170°) $[\alpha]^{25}D + 222°$ (c 0.970, ethanol). From the third band elution with chloroform-methanol (1:1) yielded 87 mg. of a mixture of dihydroepiquinine and dihydroepiquinidine. The mixture was dissolved in benzene and treated with 48 mg. of dibenzoyl-d-tartaric acid in benzene-acetone. The solvents were evaporated to dryness and the residue after recrystallization from benzene yielded the neutral dibenzoyl-d-tartrate of dihydroepiquinidine, mp 168°–170°, $[\alpha]^{25} D -13.7°$ [c 0.970, ethanol-chloroform (4:1)].

EXAMPLE 29

Tablet Formulation

|  | Per Tablet |
|---|---|
| Racemic 7'-methoxydihydrocinchonine | 25.00 mg. |
| Dicalcium Phosphate Dihydrate, unmilled | 175.00 mg. |
| Corn Starch | 24.00 mg. |
| Magnesium Stearate | 1.00 mg. |
| Total Weight | 225.00 mg. |

Procedure

25 Parts of racemic 7'-methoxy-dihydrocinchonine and 24 parts of corn starch were mixed together and passed through a No. 00 screen in Model "J" Fitzmill with hammers forward. This premix was then mixed with 175 parts of dicalcium phosphate and one-half part of magnesium stearate, passed through a No. 1A screen in Model J Fitzmill with knives forward, and slugged. The slugs were passed through a No. 2A plate in a Model "D" Fitzmill at slow speed with knives forward, and the remaining magnesium stearate was added. The mixture was mixed and compressed.

EXAMPLE 30

Capsule Formulation

|  | Per Capsule |
|---|---|
| Racemic 7'-methoxydihydrocinchonine | 50 mg. |
| Corn Starch, U.S.P. | 150 mg. |
| Talc, U.S.P. | 10 mg. |
| 7Total Weight | 210 mg. |

Procedure

Fifty parts of racemic 7'-methoxy-dihydrocinchonine were mixed with 150 parts of corn starch in a suitable mixer. The mixture was further blended by passing through a Fitzpatrick Comminuting Machine with a No. 1A screen with knives forward. The blended powder was returned to the mixer and 10 parts of talc were added and blended thoroughly. The mixture was filled into No. 4 hard shell gelatin capsules on a Parke Davis capsulating machine.

EXAMPLE 31

Suppository Formulation

|  | Per 1.3 Gm. Suppository |
|---|---|
| Racemic 7'-methoxydihydrocinchonidine | 0.025 gm. |
| Hydrogenated Coconut Oil | 1.230 gm. |
| Carnauba Wax | 0.045 gm. |

Procedure

123 Parts of hydrogenated coconut oil (Wecobee M-E. F. Drew Co., New York, New York) and 4.5 parts of carnauba wax were melted in a suitable size glass lined container (stainless steel may also be used), mixed well and cooled to 45°C. 2.5 Parts of racemic 7'-methoxydihydrocinchonidine, which had been reduced to a fine powder with no lumps, was added and stirred until completely and uniformly dispersed. The mixture was poured into suppository molds to yield suppositories having an individual weight of 1.3 gms. The suppositories were cooled and removed from molds and individually wrapped in wax paper for packaging.

We claim:

1. A racemic epimer of the formula

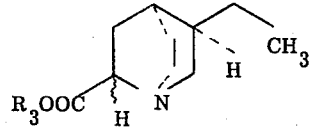

wherein $R_3$ is lower alkyl.

2. An epimer in accordance with claim 1, racemic 4,5-erythro-5-ethylquinuclidine-2 $\xi$-carboxylic acid ethyl ester.

3. An epimer in accordance with claim 1, racemic 4,5-erythro-5-ethylquinuclidine-2 $\xi$-carboxylic acid methyl ester.

4. A racemic epimer of the formula

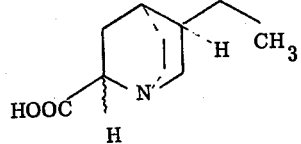

5. A racemic epimer in accordance with claim 4, 4,5-erythro-5-ethylquinuclidine-2 $\xi$-carboxylic acid.

* * * * *